(12) United States Patent
Miyake et al.

(10) Patent No.: US 7,129,064 B2
(45) Date of Patent: Oct. 31, 2006

(54) CANINE HEPATOCYTE GROWTH FACTOR

(75) Inventors: Masashi Miyake, Fukushima (JP); Shigehiro Iwabuchi, Fukushima (JP); Yasuyuki Suzuta, Fukushima (JP)

(73) Assignee: Nippon Zenyaku Kogyo Ltd., Fukushima (JP)

( * ) Notice: Subject to any disclaimer, the term of this patent is extended or adjusted under 35 U.S.C. 154(b) by 582 days.

(21) Appl. No.: 10/311,776

(22) PCT Filed: Jun. 22, 2001

(86) PCT No.: PCT/JP01/05362

§ 371 (c)(1),
(2), (4) Date: Dec. 18, 2002

(87) PCT Pub. No.: WO01/98347

PCT Pub. Date: Dec. 27, 2001

(65) Prior Publication Data

US 2003/0170685 A1   Sep. 11, 2003

(30) Foreign Application Priority Data

Jun. 22, 2000  (JP) .............................. 2000-187724

(51) Int. Cl.
*C12P 21/06* (2006.01)
(52) U.S. Cl. .................. 435/69.1; 435/325; 435/320.1; 435/252.3; 530/399; 536/23.5; 536/24.31
(58) Field of Classification Search .................... None
See application file for complete search history.

(56) References Cited

U.S. PATENT DOCUMENTS 5,342,831 A * 8/1994 Nakamura et al. ............ 514/12
5,547,856 A    8/1996 Godowski et al.

FOREIGN PATENT DOCUMENTS

| EP | 0 412 557 A1 | 2/1991 |
| EP | 0 461 560 A1 | 12/1991 |
| EP | 1291358 | 3/2003 |
| JP | 03-255096 | 11/1991 |

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells, J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Phillips, A., The challenge of gene therapy and DNA delivery. J Pharm Pharmacology 53: 1169-1174, 2001.*
Miyake et al. Canine hepatocyte growth factor: molecular cloning and characterization of the recombinant protein. Vet Immunol Immunopath 95: 135-143, 2003.*
Masato Sasaki, et al. "Identification of Mouse Mammary Fibroblast-Derived Mammary Growth Factor as Hepatocyte Growth Factor", Biochemical and Biophysical Research Communications, Mar. 1994, vol. 199, No. 2, pp. 772-779.
Youhua Liu, et al., "Molecular cloning and characterization of cDNA encoding mouse hepatocyte growth factor", Biochemica et Biophysica Acta, 1993, vol. 1216, pp. 299-303.
Kosuke Tashiro, et al., "Deduced primary structure of rat hepatocyte growth factor and expression of the mRNA in rat tissues", Proc. Natl. Acad Sci., U.S.A., Apr. 1990, vol. 87, pp. 3200-3204.
Al Okajima, et al., "Primary structure of rat hepatocyte growth factor and induction of its mRNA during liver regeneration following hepatic injury", Eur. J. Biochem., 1990, vol. 193, pp. 375-381.

(Continued)

*Primary Examiner*—Brenda Brumback
*Assistant Examiner*—Bridget E Bunner
(74) *Attorney, Agent, or Firm*—Lucas & Mercanti, LLP

(57) ABSTRACT

A canine hepatocyte growth factor gene and a 15 base pairs-deleted gene thereof encode a protein having an amino acid sequence shown in SEQ ID NO: 2 or 4 and a protein having an amino acid sequence comprising a deletion, substitution or addition of one or several amino acids and having a canine hepatocyte growth factor activity. The canine hepatocyte growth factor and the 5 amino acids-deleted canine hepatocyte growth factor are useful for the treatment of liver diseases, kidney diseases, lung diseases, digestive diseases, cardiocirculatory diseases or cranial nerve diseases.

10 Claims, 8 Drawing Sheets

OTHER PUBLICATIONS

Keiji Miyazawa, et al., "Molecular Cloning and Sequence Analysis of cDNA for Human Hepatocyte Growth Factor", Biochemical and Biophysical Research Communications, Sep. 1989, vol. 163, No. 2, pp. 967-973.

Database WPI, Section Ch, Week 199119, Derwent Publications Ltd., London, GB, class B04, AN 1991-045716, XP002348456 & JP 03 072883, Mar. 28, 1991, abstract only.

* cited by examiner cHGF PRODUCED IN COS CELL dcHGF PRODUCED IN COS CELL pCI-neo cHGF PRODUCED IN CHO CELL dcHGF PRODUCED IN CHO CELL pCI-neo 1. SILKWORM BODY FLUID INFECTED WITH cHGF RECOMBINANT VIRUS
2. SILKWORM BODY FLUID INFECTED WITH NON-RECOMBINANT VIRUS

**cHGF PRODUCED
IN SILKWORM BODY FLUID**

**SILKWORM BODY FLUID INFECTED
WITH NON-RECOMBINANT VIRUS**

1. SUPERNATANT OF Sf9 CELL INFECTED WITH cHGF RECOMBINANT VIRUS
2. SUPERNATANT OF Sf9 CELL INFECTED WITH NON-RECOMBINANT VIRUS cHGF PRODUCED IN Sf9 CELL

SUPERNATANT OF Sf9 CELL INFECTED
WITH NON-RECOMBINANT VIRUS

SEQUENCE LISTING

```
<160> NUMBER OF SEQ ID NOS: 18

<210> SEQ ID NO 1
<211> LENGTH: 2193
<212> TYPE: DNA
<213> ORGANISM: Canis familiaris
<220> FEATURE:
<221> NAME/KEY: CDS
<222> LOCATION: (1)..(2193)
<220> FEATURE:
<221> NAME/KEY: Variation
<222> LOCATION: (414)
<223> OTHER INFORMATION: r = g or a

<400> SEQUENCE: 1 atg tgg gtg acc aag ctc ctg ccc ctg ctg gtg ctg cag cag ctc ctc      48
Met Trp Val Thr Lys Leu Leu Pro Leu Leu Val Leu Gln Gln Leu Leu
  1               5                  10                  15 ctg cac ctc ctg ctg ctg ccc gtc gcc gtc ccc cgt gca gaa gga cag      96
Leu His Leu Leu Leu Leu Pro Val Ala Val Pro Arg Ala Glu Gly Gln
             20                  25                  30 aag aaa aga aga aac aca ctt cat gaa ttc aaa aag tca gca aag act     144
Lys Lys Arg Arg Asn Thr Leu His Glu Phe Lys Lys Ser Ala Lys Thr
         35                  40                  45 act cta att aaa gaa gac cca tta ctg aag ata aaa aca aaa aaa atg     192
Thr Leu Ile Lys Glu Asp Pro Leu Leu Lys Ile Lys Thr Lys Lys Met
     50                  55                  60 aac act gca gac caa tgt gcc aat aga tgt att agg aat aaa gga ctt     240
Asn Thr Ala Asp Gln Cys Ala Asn Arg Cys Ile Arg Asn Lys Gly Leu
 65                  70                  75                  80 cca ttc act tgc aag gcc ttt gtt ttt gat aaa gca agg aaa cga tgc     288
Pro Phe Thr Cys Lys Ala Phe Val Phe Asp Lys Ala Arg Lys Arg Cys
                 85                  90                  95 ctc tgg ttc cct ttc aat agc atg aca agt gga gtg aaa aaa gag ttt     336
Leu Trp Phe Pro Phe Asn Ser Met Thr Ser Gly Val Lys Lys Glu Phe
            100                 105                 110 ggt cat gaa ttt gat ctc tat gaa aac aaa gac tac att agg aac tgc     384
Gly His Glu Phe Asp Leu Tyr Glu Asn Lys Asp Tyr Ile Arg Asn Cys
```

-continued

|     |     |     |     |     | 115 |     |     |     | 120 |     |     |     |     | 125 |     |     |     |      |
|-----|-----|-----|-----|-----|-----|-----|-----|-----|-----|-----|-----|-----|-----|-----|-----|-----|-----|------|
| atc | att | ggt | aaa | gga | ggt | agc | tac | aag | ggr | aca | gtg | tct | atc | act | aag |     |     | 432  |
| Ile | Ile | Gly | Lys | Gly | Gly | Ser | Tyr | Lys | Xaa | Thr | Val | Ser | Ile | Thr | Lys |     |     |      |
|     |     | 130 |     |     |     |     | 135 |     |     |     |     | 140 |     |     |     |     |     |      |

```
agt ggc atc aaa tgc cag ccc tgg aat tcc atg ata cca cat gaa cac      480
Ser Gly Ile Lys Cys Gln Pro Trp Asn Ser Met Ile Pro His Glu His
145             150                 155                 160 agc ttt ttg cct tcg agc tat cgg ggt aaa gac cta cag gaa aac tac      528
Ser Phe Leu Pro Ser Ser Tyr Arg Gly Lys Asp Leu Gln Glu Asn Tyr
                165                 170                 175 tgt cga aat cct cga ggg gaa gaa ggg gga cct tgg tgt ttc aca agc      576
Cys Arg Asn Pro Arg Gly Glu Glu Gly Gly Pro Trp Cys Phe Thr Ser
            180                 185                 190 aat cca gag gta cgc tac gaa gtc tgt gac att cct cag tgt tca gaa      624
Asn Pro Glu Val Arg Tyr Glu Val Cys Asp Ile Pro Gln Cys Ser Glu
        195                 200                 205 gtt gaa tgc atg acc tgc aat ggg gaa agt tat cga ggt ccc atg gat      672
Val Glu Cys Met Thr Cys Asn Gly Glu Ser Tyr Arg Gly Pro Met Asp
210                 215                 220 cac aca gaa tcg ggc aag att tgt cag cgc tgg gat cat cag aca ccg      720
His Thr Glu Ser Gly Lys Ile Cys Gln Arg Trp Asp His Gln Thr Pro
225                 230                 235                 240 cac cgg cac aaa ttc ttg ccg gaa aga tat ccc gac aag ggc ttt gat      768
His Arg His Lys Phe Leu Pro Glu Arg Tyr Pro Asp Lys Gly Phe Asp
                245                 250                 255 gat aat tat tgc cgc aac cct gat ggc aag ccg agg cca tgg tgc tat      816
Asp Asn Tyr Cys Arg Asn Pro Asp Gly Lys Pro Arg Pro Trp Cys Tyr
            260                 265                 270 act ctt gac cct gac acc ccc tgg gag tac tgt gca att aaa atg tgt      864
Thr Leu Asp Pro Asp Thr Pro Trp Glu Tyr Cys Ala Ile Lys Met Cys
        275                 280                 285 gct cac agt act atg aat gat aca gat gtc cct atg gaa aca act gaa      912
Ala His Ser Thr Met Asn Asp Thr Asp Val Pro Met Glu Thr Thr Glu
290                 295                 300 tgc att caa ggt caa gga gaa ggt tac cgg ggc acc atc aat acc att      960
Cys Ile Gln Gly Gln Gly Glu Gly Tyr Arg Gly Thr Ile Asn Thr Ile
305                 310                 315                 320 tgg aat gga gtt ccg tgt cag cgt tgg gat tcc cag tat cct cac cag     1008
Trp Asn Gly Val Pro Cys Gln Arg Trp Asp Ser Gln Tyr Pro His Gln
                325                 330                 335 cat gac ata act cct gaa aat ttc aag tgc aag gac cta aga gaa aat     1056
His Asp Ile Thr Pro Glu Asn Phe Lys Cys Lys Asp Leu Arg Glu Asn
            340                 345                 350 tat tgc cga aat cca gat ggg gct gag tca ccc tgg tgt ttt acc act     1104
Tyr Cys Arg Asn Pro Asp Gly Ala Glu Ser Pro Trp Cys Phe Thr Thr
        355                 360                 365 gat cca aac atc cga gtt ggc tac tgc tcc caa att cca aaa tgt gat     1152
Asp Pro Asn Ile Arg Val Gly Tyr Cys Ser Gln Ile Pro Lys Cys Asp
370                 375                 380 gtg tca agt gga caa gat tgt tat cgg ggg aat ggc aaa aat tat atg     1200
Val Ser Ser Gly Gln Asp Cys Tyr Arg Gly Asn Gly Lys Asn Tyr Met
385                 390                 395                 400 ggc aat tta tcc aaa aca cga tct gga cta aca tgt tca atg tgg gag     1248
Gly Asn Leu Ser Lys Thr Arg Ser Gly Leu Thr Cys Ser Met Trp Glu
                405                 410                 415 aag aac atg gaa gac tta cat agg cat atc ttc tgg gaa cca gat gct     1296
Lys Asn Met Glu Asp Leu His Arg His Ile Phe Trp Glu Pro Asp Ala
            420                 425                 430 agt aag ctg aat aag aat tac tgc cgg aat cct gat gac gat gcc cat     1344
```

-continued

```
Ser Lys Leu Asn Lys Asn Tyr Cys Arg Asn Pro Asp Asp Ala His
        435                 440                 445 ggt ccc tgg tgt tac acg gga aat cct ctc att cca tgg gat tat tgt    1392
Gly Pro Trp Cys Tyr Thr Gly Asn Pro Leu Ile Pro Trp Asp Tyr Cys
450                 455                 460 cct att ttt cgt tgt gaa ggt gat acc aca cct aca ata gtc aat tta    1440
Pro Ile Phe Arg Cys Glu Gly Asp Thr Thr Pro Thr Ile Val Asn Leu
465                 470                 475                 480 gac cat cct gta ata tct tgt gcc aaa aca aaa caa tta cga gtt gta    1488
Asp His Pro Val Ile Ser Cys Ala Lys Thr Lys Gln Leu Arg Val Val
                485                 490                 495 aat gga att cca aca cgg act aat gta gga tgg atg gtt agt ttg aaa    1536
Asn Gly Ile Pro Thr Arg Thr Asn Val Gly Trp Met Val Ser Leu Lys
            500                 505                 510 tac aga aat aaa cat atc tgt gga gga tca ttg ata aag gaa agt tgg    1584
Tyr Arg Asn Lys His Ile Cys Gly Gly Ser Leu Ile Lys Glu Ser Trp
        515                 520                 525 att ctt act gca aga caa tgt ttc ccc tct cga aac aga gac ttg aaa    1632
Ile Leu Thr Ala Arg Gln Cys Phe Pro Ser Arg Asn Arg Asp Leu Lys
    530                 535                 540 gat tat gaa gct tgg ctt ggg att cat gac gtc cac gga aaa gga gat    1680
Asp Tyr Glu Ala Trp Leu Gly Ile His Asp Val His Gly Lys Gly Asp
545                 550                 555                 560 gag aaa cgc aaa cag gtt ctg aat gtt tcc cag ctg gta tat ggg cct    1728
Glu Lys Arg Lys Gln Val Leu Asn Val Ser Gln Leu Val Tyr Gly Pro
                565                 570                 575 gaa gga tca gat ctg gta tta ctg aag ctt gct agg ccc gct atc ctg    1776
Glu Gly Ser Asp Leu Val Leu Leu Lys Leu Ala Arg Pro Ala Ile Leu
            580                 585                 590 gat gat ttt gtt agt aca atc gat tta cct aat tat gga tgc acc att    1824
Asp Asp Phe Val Ser Thr Ile Asp Leu Pro Asn Tyr Gly Cys Thr Ile
        595                 600                 605 cct gaa aaa acc act tgc agt gtt tat ggc tgg ggt tat act gga tcg    1872
Pro Glu Lys Thr Thr Cys Ser Val Tyr Gly Trp Gly Tyr Thr Gly Ser
    610                 615                 620 atc aac ttt gat ggt cta tta cga gta gca cat ctc tat att atg ggg    1920
Ile Asn Phe Asp Gly Leu Leu Arg Val Ala His Leu Tyr Ile Met Gly
625                 630                 635                 640 aat gag aaa tgc agc caa tac cat caa ggg aag gtg aca ctg aat gag    1968
Asn Glu Lys Cys Ser Gln Tyr His Gln Gly Lys Val Thr Leu Asn Glu
                645                 650                 655 tct gaa ata tgt gct gga gct gaa aat att gta tca gga cca tgt gag    2016
Ser Glu Ile Cys Ala Gly Ala Glu Asn Ile Val Ser Gly Pro Cys Glu
            660                 665                 670 gga gat tat ggt ggc cca ctt gtt tgc gaa caa cat aaa atg agg atg    2064
Gly Asp Tyr Gly Gly Pro Leu Val Cys Glu Gln His Lys Met Arg Met
        675                 680                 685 gtt ctt ggc gtc att gtt cct ggt cgt gga tgt gcc att cca aat cgt    2112
Val Leu Gly Val Ile Val Pro Gly Arg Gly Cys Ala Ile Pro Asn Arg
    690                 695                 700 cct ggc att ttt gtc cga gta gca tat tat gca aaa tgg ata cac aaa    2160
Pro Gly Ile Phe Val Arg Val Ala Tyr Tyr Ala Lys Trp Ile His Lys
705                 710                 715                 720 att ata tta acg tat aag ata caa cag tca tag                        2193
Ile Ile Leu Thr Tyr Lys Ile Gln Gln Ser
                725                 730

<210> SEQ ID NO 2
<211> LENGTH: 730
<212> TYPE: PRT
```

```
<213> ORGANISM: Canis familiaris
<220> FEATURE:
<221> NAME/KEY: Variation
<222> LOCATION: (138)
<223> OTHER INFORMATION: Xaa = Gly

<400> SEQUENCE: 2
```

| | | | | | | | | | | | | | | |
|---|---|---|---|---|---|---|---|---|---|---|---|---|---|---|
| Met | Trp | Val | Thr | Lys | Leu | Leu | Pro | Leu | Leu | Val | Leu | Gln | Gln | Leu | Leu |
| 1 | | | | 5 | | | | | 10 | | | | | 15 | |

| Leu | His | Leu | Leu | Leu | Leu | Pro | Val | Ala | Val | Pro | Arg | Ala | Glu | Gly | Gln |
| | | | 20 | | | | | 25 | | | | | 30 | | |

| Lys | Lys | Arg | Arg | Asn | Thr | Leu | His | Glu | Phe | Lys | Ser | Ala | Lys | Thr |
| | | 35 | | | | | 40 | | | | | 45 | | |

| Thr | Leu | Ile | Lys | Glu | Asp | Pro | Leu | Leu | Lys | Ile | Lys | Thr | Lys | Lys | Met |
| | 50 | | | | | 55 | | | | | 60 | | | | |

| Asn | Thr | Ala | Asp | Gln | Cys | Ala | Asn | Arg | Cys | Ile | Arg | Asn | Lys | Gly | Leu |
| 65 | | | | | 70 | | | | | 75 | | | | | 80 |

| Pro | Phe | Thr | Cys | Lys | Ala | Phe | Val | Phe | Asp | Lys | Ala | Arg | Lys | Arg | Cys |
| | | | | 85 | | | | | 90 | | | | | 95 | |

| Leu | Trp | Phe | Pro | Phe | Asn | Ser | Met | Thr | Ser | Gly | Val | Lys | Lys | Glu | Phe |
| | | | 100 | | | | | 105 | | | | | 110 | | |

| Gly | His | Glu | Phe | Asp | Leu | Tyr | Glu | Asn | Lys | Asp | Tyr | Ile | Arg | Asn | Cys |
| | | | 115 | | | | | 120 | | | | | 125 | | |

| Ile | Ile | Gly | Lys | Gly | Gly | Ser | Tyr | Lys | Xaa | Thr | Val | Ser | Ile | Thr | Lys |
| | 130 | | | | | 135 | | | | | 140 | | | | |

| Ser | Gly | Ile | Lys | Cys | Gln | Pro | Trp | Asn | Ser | Met | Ile | Pro | His | Glu | His |
| 145 | | | | | 150 | | | | | 155 | | | | | 160 |

| Ser | Phe | Leu | Pro | Ser | Ser | Tyr | Arg | Gly | Lys | Asp | Leu | Gln | Glu | Asn | Tyr |
| | | | | 165 | | | | | 170 | | | | | 175 | |

| Cys | Arg | Asn | Pro | Arg | Gly | Glu | Glu | Gly | Gly | Pro | Trp | Cys | Phe | Thr | Ser |
| | | | 180 | | | | | 185 | | | | | 190 | | |

| Asn | Pro | Glu | Val | Arg | Tyr | Glu | Val | Cys | Asp | Ile | Pro | Gln | Cys | Ser | Glu |
| | | | 195 | | | | | 200 | | | | | 205 | | |

| Val | Glu | Cys | Met | Thr | Cys | Asn | Gly | Glu | Ser | Tyr | Arg | Gly | Pro | Met | Asp |
| | 210 | | | | | 215 | | | | | 220 | | | | |

| His | Thr | Glu | Ser | Gly | Lys | Ile | Cys | Gln | Arg | Trp | Asp | His | Gln | Thr | Pro |
| 225 | | | | | 230 | | | | | 235 | | | | | 240 |

| His | Arg | His | Lys | Phe | Leu | Pro | Glu | Arg | Tyr | Pro | Asp | Lys | Gly | Phe | Asp |
| | | | | 245 | | | | | 250 | | | | | 255 | |

| Asp | Asn | Tyr | Cys | Arg | Asn | Pro | Asp | Gly | Lys | Pro | Arg | Pro | Trp | Cys | Tyr |
| | | | 260 | | | | | 265 | | | | | 270 | | |

| Thr | Leu | Asp | Pro | Asp | Thr | Pro | Trp | Glu | Tyr | Cys | Ala | Ile | Lys | Met | Cys |
| | | | 275 | | | | | 280 | | | | | 285 | | |

| Ala | His | Ser | Thr | Met | Asn | Asp | Thr | Asp | Val | Pro | Met | Glu | Thr | Thr | Glu |
| | 290 | | | | | 295 | | | | | 300 | | | | |

| Cys | Ile | Gln | Gly | Gln | Gly | Glu | Gly | Tyr | Arg | Gly | Thr | Ile | Asn | Thr | Ile |
| 305 | | | | | 310 | | | | | 315 | | | | | 320 |

| Trp | Asn | Gly | Val | Pro | Cys | Gln | Arg | Trp | Asp | Ser | Gln | Tyr | Pro | His | Gln |
| | | | | 325 | | | | | 330 | | | | | 335 | |

| His | Asp | Ile | Thr | Pro | Glu | Asn | Phe | Lys | Cys | Lys | Asp | Leu | Arg | Glu | Asn |
| | | | 340 | | | | | 345 | | | | | 350 | | |

| Tyr | Cys | Arg | Asn | Pro | Asp | Gly | Ala | Glu | Ser | Pro | Trp | Cys | Phe | Thr | Thr |
| | | | 355 | | | | | 360 | | | | | 365 | | |

| Asp | Pro | Asn | Ile | Arg | Val | Gly | Tyr | Cys | Ser | Gln | Ile | Pro | Lys | Cys | Asp |
| | | | 370 | | | | | 375 | | | | | 380 | | |

-continued

```
Val Ser Ser Gly Gln Asp Cys Tyr Arg Gly Asn Gly Lys Asn Tyr Met
385                 390                 395                 400

Gly Asn Leu Ser Lys Thr Arg Ser Gly Leu Thr Cys Ser Met Trp Glu
            405                 410                 415

Lys Asn Met Glu Asp Leu His Arg His Ile Phe Trp Glu Pro Asp Ala
        420                 425                 430

Ser Lys Leu Asn Lys Asn Tyr Cys Arg Asn Pro Asp Asp Ala His
    435                 440                 445

Gly Pro Trp Cys Tyr Thr Gly Asn Pro Leu Ile Pro Trp Asp Tyr Cys
    450                 455                 460

Pro Ile Phe Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Val Gly Trp Met Val Ser Leu Lys
            500                 505                 510

Tyr Arg Asn Lys His Ile Cys Gly Gly Ser Leu Ile Lys Glu Ser Trp
        515                 520                 525

Ile Leu Thr Ala Arg Gln Cys Phe Pro Ser Arg Asn Arg Asp Leu Lys
    530                 535                 540

Asp Tyr Glu Ala Trp Leu Gly Ile His Asp Val His Gly Lys Gly Asp
545                 550                 555                 560

Glu Lys Arg Lys Gln Val Leu Asn Val Ser Gln Leu Val Tyr Gly Pro
                565                 570                 575

Glu Gly Ser Asp Leu Val Leu Leu Lys Leu Ala Arg Pro Ala Ile Leu
            580                 585                 590

Asp Asp Phe Val Ser Thr Ile Asp Leu Pro Asn Tyr Gly Cys Thr Ile
        595                 600                 605

Pro Glu Lys Thr Thr Cys Ser Val Tyr Gly Trp Gly Tyr Thr Gly Ser
    610                 615                 620

Ile Asn Phe Asp Gly Leu Leu Arg Val Ala His Leu Tyr Ile Met Gly
625                 630                 635                 640

Asn Glu Lys Cys Ser Gln Tyr His Gln Gly Lys Val Thr Leu Asn Glu
                645                 650                 655

Ser Glu Ile Cys Ala Gly Ala Glu Asn Ile Val Ser Gly Pro Cys Glu
            660                 665                 670

Gly Asp Tyr Gly Gly Pro Leu Val Cys Glu Gln His Lys Met Arg Met
        675                 680                 685

Val Leu Gly Val Ile Val Pro Gly Arg Gly Cys Ala Ile Pro Asn Arg
    690                 695                 700

Pro Gly Ile Phe Val Arg Val Ala Tyr Tyr Ala Lys Trp Ile His Lys
705                 710                 715                 720

Ile Ile Leu Thr Tyr Lys Ile Gln Gln Ser
                725                 730

<210> SEQ ID NO 3
<211> LENGTH: 2178
<212> TYPE: DNA
<213> ORGANISM: Canis familiaris
<220> FEATURE:
<221> NAME/KEY: CDS
<222> LOCATION: (1)..(2178)
<220> FEATURE:
<221> NAME/KEY: Variation
<222> LOCATION: (414)
<223> OTHER INFORMATION: r = g or a
```

<400> SEQUENCE: 3

```
atg tgg gtg acc aag ctc ctg ccc ctg ctg gtg ctg cag cag ctc ctc      48
Met Trp Val Thr Lys Leu Leu Pro Leu Leu Val Leu Gln Gln Leu Leu
 1               5                  10                  15 ctg cac ctc ctc ctg ctg ccc gtc gcc gtc ccc cgt gca gaa gga cag      96
Leu His Leu Leu Leu Leu Pro Val Ala Val Pro Arg Ala Glu Gly Gln
                20                  25                  30 aag aaa aga aga aac aca ctt cat gaa ttc aaa aag tca gca aag act     144
Lys Lys Arg Arg Asn Thr Leu His Glu Phe Lys Lys Ser Ala Lys Thr
        35                  40                  45 act cta att aaa gaa gac cca tta ctg aag ata aaa aca aaa aaa atg     192
Thr Leu Ile Lys Glu Asp Pro Leu Leu Lys Ile Lys Thr Lys Lys Met
 50                  55                  60 aac act gca gac caa tgt gcc aat aga tgt att agg aat aaa gga ctt     240
Asn Thr Ala Asp Gln Cys Ala Asn Arg Cys Ile Arg Asn Lys Gly Leu
 65                  70                  75                  80 cca ttc act tgc aag gcc ttt gtt ttt gat aaa gca agg aaa cga tgc     288
Pro Phe Thr Cys Lys Ala Phe Val Phe Asp Lys Ala Arg Lys Arg Cys
                85                  90                  95 ctc tgg ttc cct ttc aat agc atg aca agt gga gtg aaa aaa gag ttt     336
Leu Trp Phe Pro Phe Asn Ser Met Thr Ser Gly Val Lys Lys Glu Phe
            100                 105                 110 ggt cat gaa ttt gat ctc tat gaa aac aaa gac tac att agg aac tgc     384
Gly His Glu Phe Asp Leu Tyr Glu Asn Lys Asp Tyr Ile Arg Asn Cys
        115                 120                 125 atc att ggt aaa gga ggt agc tac aag ggr aca gtg tct atc act aag     432
Ile Ile Gly Lys Gly Gly Ser Tyr Lys Xaa Thr Val Ser Ile Thr Lys
130                 135                 140 agt ggc atc aaa tgc cag ccc tgg aat tcc atg ata cca cat gaa cac     480
Ser Gly Ile Lys Cys Gln Pro Trp Asn Ser Met Ile Pro His Glu His
145                 150                 155                 160 agc tat cgg ggt aaa gac cta cag gaa aac tac tgt cga aat cct cga     528
Ser Tyr Arg Gly Lys Asp Leu Gln Glu Asn Tyr Cys Arg Asn Pro Arg
                165                 170                 175 ggg gaa gaa ggg gga cct tgg tgt ttc aca agc aat cca gag gta cgc     576
Gly Glu Glu Gly Gly Pro Trp Cys Phe Thr Ser Asn Pro Glu Val Arg
            180                 185                 190 tac gaa gtc tgt gac att cct cag tgt tca gaa gtt gaa tgc atg acc     624
Tyr Glu Val Cys Asp Ile Pro Gln Cys Ser Glu Val Glu Cys Met Thr
        195                 200                 205 tgc aat ggg gaa agt tat cga ggt ccc atg gat cac aca gaa tcg ggc     672
Cys Asn Gly Glu Ser Tyr Arg Gly Pro Met Asp His Thr Glu Ser Gly
210                 215                 220 aag att tgt cag cgc tgg gat cat cag aca ccg cac gg cac aaa ttc     720
Lys Ile Cys Gln Arg Trp Asp His Gln Thr Pro His Arg His Lys Phe
225                 230                 235                 240 ttg ccg gaa aga tat ccc gac aag ggc ttt gat gat aat tat tgc cgc     768
Leu Pro Glu Arg Tyr Pro Asp Lys Gly Phe Asp Asp Asn Tyr Cys Arg
                245                 250                 255 aac cct gat ggc aag ccg agg cca tgg tgc tat act ctt gac cct gac     816
Asn Pro Asp Gly Lys Pro Arg Pro Trp Cys Tyr Thr Leu Asp Pro Asp
            260                 265                 270 acc ccc tgg gag tac tgt gca att aaa atg tgt gct cac agt act atg     864
Thr Pro Trp Glu Tyr Cys Ala Ile Lys Met Cys Ala His Ser Thr Met
        275                 280                 285 aat gat aca gat gtc cct atg gaa aca act gaa tgc att caa ggt caa     912
Asn Asp Thr Asp Val Pro Met Glu Thr Thr Glu Cys Ile Gln Gly Gln
290                 295                 300
```

-continued

| | | |
|---|---|---|
| gga gaa ggt tac cgg ggc acc atc aat acc att tgg aat gga gtt ccg<br>Gly Glu Gly Tyr Arg Gly Thr Ile Asn Thr Ile Trp Asn Gly Val Pro<br>305                        310                        315                        320 | 960 |
| tgt cag cgt tgg gat tcc cag tat cct cac cag cat gac ata act cct<br>Cys Gln Arg Trp Asp Ser Gln Tyr Pro His Gln His Asp Ile Thr Pro<br>                        325                        330                        335 | 1008 |
| gaa aat ttc aag tgc aag gac cta aga gaa aat tat tgc cga aat cca<br>Glu Asn Phe Lys Cys Lys Asp Leu Arg Glu Asn Tyr Cys Arg Asn Pro<br>                340                        345                        350 | 1056 |
| gat ggg gct gag tca ccc tgg tgt ttt acc act gat cca aac atc cga<br>Asp Gly Ala Glu Ser Pro Trp Cys Phe Thr Thr Asp Pro Asn Ile Arg<br>        355                        360                        365 | 1104 |
| gtt ggc tac tgc tcc caa att cca aaa tgt gat gtg tca agt gga caa<br>Val Gly Tyr Cys Ser Gln Ile Pro Lys Cys Asp Val Ser Ser Gly Gln<br>370                        375                        380 | 1152 |
| gat tgt tat cgg ggg aat ggc aaa aat tat atg ggc aat tta tcc aaa<br>Asp Cys Tyr Arg Gly Asn Gly Lys Asn Tyr Met Gly Asn Leu Ser Lys<br>385                        390                        395                        400 | 1200 |
| aca cga tct gga cta aca tgt tca atg tgg gag aag aac atg gaa gac<br>Thr Arg Ser Gly Leu Thr Cys Ser Met Trp Glu Lys Asn Met Glu Asp<br>                            405                        410                        415 | 1248 |
| tta cat agg cat atc ttc tgg gaa cca gat gct agt aag ctg aat aag<br>Leu His Arg His Ile Phe Trp Glu Pro Asp Ala Ser Lys Leu Asn Lys<br>                420                        425                        430 | 1296 |
| aat tac tgc cgg aat cct gat gac gat gcc cat ggt ccc tgg tgt tac<br>Asn Tyr Cys Arg Asn Pro Asp Asp Asp Ala His Gly Pro Trp Cys Tyr<br>        435                        440                        445 | 1344 |
| acg gga aat cct ctc att cca tgg gat tat tgt cct att ttt cgt tgt<br>Thr Gly Asn Pro Leu Ile Pro Trp Asp Tyr Cys Pro Ile Phe Arg Cys<br>450                        455                        460 | 1392 |
| gaa ggt gat acc aca cct aca ata gtc aat tta gac cat cct gta ata<br>Glu Gly Asp Thr Thr Pro Thr Ile Val Asn Leu Asp His Pro Val Ile<br>465                        470                        475                        480 | 1440 |
| tct tgt gcc aaa aca aaa caa tta cga gtt gta aat gga att cca aca<br>Ser Cys Ala Lys Thr Lys Gln Leu Arg Val Val Asn Gly Ile Pro Thr<br>                            485                        490                        495 | 1488 |
| cgg act aat gta gga tgg atg gtt agt ttg aaa tac aga aat aaa cat<br>Arg Thr Asn Val Gly Trp Met Val Ser Leu Lys Tyr Arg Asn Lys His<br>                500                        505                        510 | 1536 |
| atc tgt gga gga tca ttg ata aag gaa agt tgg att ctt act gca aga<br>Ile Cys Gly Gly Ser Leu Ile Lys Glu Ser Trp Ile Leu Thr Ala Arg<br>        515                        520                        525 | 1584 |
| caa tgt ttc ccc tct cga aac aga gac ttg aaa gat tat gaa gct tgg<br>Gln Cys Phe Pro Ser Arg Asn Arg Asp Leu Lys Asp Tyr Glu Ala Trp<br>530                        535                        540 | 1632 |
| ctt ggg att cat gac gtc cac gga aaa gga gat gag aaa cgc aaa cag<br>Leu Gly Ile His Asp Val His Gly Lys Gly Asp Glu Lys Arg Lys Gln<br>545                        550                        555                        560 | 1680 |
| gtt ctg aat gtt tcc cag ctg gta tat ggg cct gaa gga tca gat ctg<br>Val Leu Asn Val Ser Gln Leu Val Tyr Gly Pro Glu Gly Ser Asp Leu<br>                            565                        570                        575 | 1728 |
| gta tta ctg aag ctt gct agg ccc gct atc ctg gat gat ttt gtt agt<br>Val Leu Leu Lys Leu Ala Arg Pro Ala Ile Leu Asp Asp Phe Val Ser<br>                580                        585                        590 | 1776 |
| aca atc gat tta cct aat tat gga tgc acc att cct gaa aaa acc act<br>Thr Ile Asp Leu Pro Asn Tyr Gly Cys Thr Ile Pro Glu Lys Thr Thr<br>        595                        600                        605 | 1824 |
| tgc agt gtt tat ggc tgg ggt tat act gga tcg atc aac ttt gat ggt<br>Cys Ser Val Tyr Gly Trp Gly Tyr Thr Gly Ser Ile Asn Phe Asp Gly<br>610                        615                        620 | 1872 |

```
cta tta cga gta gca cat ctc tat att atg ggg aat gag aaa tgc agc      1920
Leu Leu Arg Val Ala His Leu Tyr Ile Met Gly Asn Glu Lys Cys Ser
625                 630                 635                 640 caa tac cat caa ggg aag gtg aca ctg aat gag tct gaa ata tgt gct      1968
Gln Tyr His Gln Gly Lys Val Thr Leu Asn Glu Ser Glu Ile Cys Ala
            645                 650                 655 gga gct gaa aat att gta tca gga cca tgt gag gga gat tat ggt ggc      2016
Gly Ala Glu Asn Ile Val Ser Gly Pro Cys Glu Gly Asp Tyr Gly Gly
            660                 665                 670 cca ctt gtt tgc gaa caa cat aaa atg agg atg gtt ctt ggc gtc att      2064
Pro Leu Val Cys Glu Gln His Lys Met Arg Met Val Leu Gly Val Ile
            675                 680                 685 gtt cct ggt cgt gga tgt gcc att cca aat cgt cct ggc att ttt gtc      2112
Val Pro Gly Arg Gly Cys Ala Ile Pro Asn Arg Pro Gly Ile Phe Val
690                 695                 700 cga gta gca tat tat gca aaa tgg ata cac aaa att ata tta acg tat      2160
Arg Val Ala Tyr Tyr Ala Lys Trp Ile His Lys Ile Ile Leu Thr Tyr
705                 710                 715                 720 aag ata caa cag tca tag                                              2178
Lys Ile Gln Gln Ser
                725

<210> SEQ ID NO 4
<211> LENGTH: 725
<212> TYPE: PRT
<213> ORGANISM: Canis familiaris
<220> FEATURE:
<221> NAME/KEY: Variation
<222> LOCATION: (138)
<223> OTHER INFORMATION: Xaa = Gly

<400> SEQUENCE: 4

Met Trp Val Thr Lys Leu Leu Pro Leu Leu Val Leu Gln Gln Leu Leu
 1               5                  10                  15

Leu His Leu Leu Leu Leu Pro Val Ala Val Pro Arg Ala Glu Gly Gln
                20                  25                  30

Lys Lys Arg Arg Asn Thr Leu His Glu Phe Lys Lys Ser Ala Lys Thr
            35                  40                  45

Thr Leu Ile Lys Glu Asp Pro Leu Leu Lys Ile Lys Thr Lys Lys Met
        50                  55                  60

Asn Thr Ala Asp Gln Cys Ala Asn Arg Cys Ile Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Thr Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Gly Ser Tyr Lys Xaa Thr Val Ser Ile Thr Lys
    130                 135                 140

Ser Gly Ile Lys Cys Gln Pro Trp Asn Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205
```

-continued

```
Cys Asn Gly Glu Ser Tyr Arg Gly Pro Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asn Tyr Cys Arg
                    245                 250                 255

Asn Pro Asp Gly Lys Pro Arg Pro Trp Cys Tyr Thr Leu Asp Pro Asp
                260                 265                 270

Thr Pro Trp Glu Tyr Cys Ala Ile Lys Met Cys Ala His Ser Thr Met
        275                 280                 285

Asn Asp Thr Asp Val Pro Met Glu Thr Thr Glu Cys Ile Gln Gly Gln
    290                 295                 300

Gly Glu Gly Tyr Arg Gly Thr Ile Asn Thr Ile Trp Asn Gly Val Pro
305                 310                 315                 320

Cys Gln Arg Trp Asp Ser Gln Tyr Pro His Gln His Asp Ile Thr Pro
                325                 330                 335

Glu Asn Phe Lys Cys Lys Asp Leu Arg Glu Asn Tyr Cys Arg Asn Pro
                340                 345                 350

Asp Gly Ala Glu Ser Pro Trp Cys Phe Thr Thr Asp Pro Asn Ile Arg
            355                 360                 365

Val Gly Tyr Cys Ser Gln Ile Pro Lys Cys Asp Val Ser Ser Gly Gln
    370                 375                 380

Asp Cys Tyr Arg Gly Asn Gly Lys Asn Tyr Met Gly Asn Leu Ser Lys
385                 390                 395                 400

Thr Arg Ser Gly Leu Thr Cys Ser Met Trp Glu Lys Asn Met Glu Asp
                405                 410                 415

Leu His Arg His Ile Phe Trp Glu Pro Asp Ala Ser Lys Leu Asn Lys
                420                 425                 430

Asn Tyr Cys Arg Asn Pro Asp Asp Ala His Gly Pro Trp Cys Tyr
            435                 440                 445

Thr Gly Asn Pro Leu Ile Pro Trp Asp Tyr Cys Pro Ile Phe Arg Cys
450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Val Gly Trp Met Val Ser Leu Lys Tyr Arg Asn Lys His
                500                 505                 510

Ile Cys Gly Gly Ser Leu Ile Lys Glu Ser Trp Ile Leu Thr Ala Arg
            515                 520                 525

Gln Cys Phe Pro Ser Arg Asn Arg Asp Leu Lys Asp Tyr Glu Ala Trp
    530                 535                 540

Leu Gly Ile His Asp Val His Gly Lys Gly Asp Glu Lys Arg Lys Gln
545                 550                 555                 560

Val Leu Asn Val Ser Gln Leu Val Tyr Gly Pro Glu Gly Ser Asp Leu
                565                 570                 575

Val Leu Leu Lys Leu Ala Arg Pro Ala Ile Leu Asp Asp Phe Val Ser
            580                 585                 590

Thr Ile Asp Leu Pro Asn Tyr Gly Cys Thr Ile Pro Glu Lys Thr Thr
        595                 600                 605

Cys Ser Val Tyr Gly Trp Gly Tyr Thr Gly Ser Ile Asn Phe Asp Gly
    610                 615                 620
```

```
Leu Leu Arg Val Ala His Leu Tyr Ile Met Gly Asn Glu Lys Cys Ser
625                 630                 635                 640

Gln Tyr His Gln Gly Lys Val Thr Leu Asn Glu Ser Glu Ile Cys Ala
            645                 650                 655

Gly Ala Glu Asn Ile Val Ser Gly Pro Cys Glu Gly Asp Tyr Gly Gly
                660                 665                 670

Pro Leu Val Cys Glu Gln His Lys Met Arg Met Val Leu Gly Val Ile
            675                 680                 685

Val Pro Gly Arg Gly Cys Ala Ile Pro Asn Arg Pro Gly Ile Phe Val
        690                 695                 700

Arg Val Ala Tyr Tyr Ala Lys Trp Ile His Lys Ile Ile Leu Thr Tyr
705                 710                 715                 720

Lys Ile Gln Gln Ser
                725

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 5
ccatgaattt gacctctatg                                              20

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:Synthetic

<400> SEQUENCE: 6
tgtgtatcca ttttgcataa tatgctactc                                   30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:Synthetic

<400> SEQUENCE: 7
atgcagccaa taccatcaag ggaaggtgac                                   30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Synthetic

<400> SEQUENCE: 8
tcaggaccat gtgagggaga ttatggtggc                                   30

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:Synthetic

<400> SEQUENCE: 9
```

```
cttcgtagcg tacctctgga ttgcttgtg                                              29

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 10
ttccagggct ggcatttgat gccactc                                                27

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Synthetic

<400> SEQUENCE: 11
ggccttgcaa gtgaatggaa gtcc                                                   24

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 12
acggcgacgg gcagcaggag gaggtgc                                                27

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 13
atgtgggtga ccaagctcc                                                         19

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 14
tgggtgcttc agacacactt acatcag                                                27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 15
atgtgggtga ccaagctcct gccctg                                                 27

<210> SEQ ID NO 16
<211> LENGTH: 27
<212> TYPE: DNA
<213> ORGANISM: Artificial Sequence
```

```
<220> FEATURE:
<223> OTHER INFORMATION: Description of Artificial Sequence:Synthetic

<400> SEQUENCE: 16
ctatgactgt tgtatcttat acgttaa                                           27

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 17
ctatcactaa gagtggcatc                                                   20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 18
ggaatgtcac agacttcgta g                                                 21
```

CANINE HEPATOCYTE GROWTH FACTOR

This patent application claims a benefit of priority from Japanese Patent Application No. 2000/187724 filed Jun. 22, 2000 through PCT/JP01/05362 filed Jun. 22, 2001; the contents of each of which are incorporated herein by reference.

FIELD OF THE INVENTION

The present invention relates to a canine hepatocyte growth factor, a 5 amino acids-deleted canine hepatocyte growth factor thereof, and genes encoding these factors.

BACKGROUND OF THE INVENTION

Human hepatocyte growth factor (hereinafter refer to as "HGF") has been purified as a liver regeneration factor. A gene encoding this factor has also been cloned and the sequence has been determined. Initially, HGF had been considered to function only for hepatocyte growth. However, subsequent studies have revealed that HGF does not only function for growth and regeneration of a hepatocyte, but also has strong effects of protecting from damage and of regenerating an organ on lung, kidney, blood vessel and heart tissues. Moreover, HGF also has very varied functions, for example it shows a strong antitumor activity against certain types of cancer.

From a study using various types of cultured cells, it has been found that HGF functions as a growth promoting factor, a mobility promoting factor, a morphogenesis promoting factor and a tumor suppressing factor. Moreover, expression of HGF enhances in organs, such as the lung and the kidney, responses to hepatopathy, and regeneration of the liver is promoted by a mechanism via the blood. It has been confirmed that, in other organs such as the kidney or the lung also, regeneration of such organs is promoted by the same mechanism. All of these HGF functions are biological activities essential for the construction and maintenance of tissues and organs, and so it is expected that HGF would be clinically significant when applied as specific medicines for intractable organ diseases for which basic treatment methods have not yet been established. Furthermore, a gene therapy for chronic arteriosclerosis obliterans of diabetes patients, which uses an HGF gene, is being attempted.

It has been reported that HGF has many variants generated by alternative splicing. It has been shown that, of these, a variant HGF which lacks 15 base pairs in the first kringle domain corresponding to a receptor binding site, that is, a variant HGF which lacks 5 amino acids, has a two or three times higher growth promoting activity on epithelium cells, when compared with ordinary HGF, and that this variant HGF has a different physiological action. It is hoped that this 15 base pairs-deleted HGF has a higher treatment effect on diseases mainly such as damaged epithelial tissues.

A mechanism for regenerating liver tissues by HGF will be described in detail. The expression of HGF mRNA is induced promptly in an interstitial cell, such as the Kupffer cell or the sinusoid endothelial cell in the liver, in response to various types of hepatopathies. HGF produced and secreted from interstitial cells acts on an epithelial cell such as a hepatocyte or biliary cell and promotes regeneration of the liver. Experiments have been carried out where recombinant HGF was administered to a disease model animal, and it has been reported that the recombinant HGF regenerated many types of organopathy. It has been reported that the tissues of many impaired organs such as the liver (e.g. hepatocirrhosis, hepatitis, fatty liver disease, etc.), the kidney (acute and chronic renal failure), the lung, the heart and the stomach, have been regenerated.

The full length of a human HGF gene (hereinafter, referred to as "hHGF") spans about 70 kb. The full length of mRNA, which is a transcribed product of the hHGF gene, is about 6 kb, and the length of a region encoding a protein in the mRNA is about 2.2 kb. The hHGF is initially synthesized as a single prepro-HGF consisting of 728 amino acids, and after 31 amino acids existing at the N-terminus are cleaved, a portion between the $494^{th}$ Arg and the $495^{th}$ Val is cleaved with protease, so that it becomes a mature molecule in which the α and β chains link with a single difulfide bond.

Thus far, HGF genes of human, mouse, rat and so on have been cloned, and the nucleotide sequences thereof have been determined.

With the recent trend of the aging of household pets, there occurs a problem regarding increases of various atrophic or regressive canine diseases, which are associated with aging. The development of pharmaceuticals directed towards such diseases, in which the regeneration of tissues are required, is considered to be important. Generally, these diseases often become chronic. Long-term administration of medicine is required to treat chronic diseases. However, if recombinant HGF proteins are administered to different species, the problem of antigenicity occurs and there may be a risk that long-term administration becomes impossible. Therefore, a recombinant canine HGF, which does not have the problem of antigenicity and can be administered for a long time, is required as a therapeutic agent for these chronic canine diseases.

OBJECT AND SUMMARY OF THE INVENTION

It is an object of the present invention to provide a canine HGF, a 15 base pairs-deleted HGF thereof, and genes encoding the canine HGF and the 15 base pairs-deleted HGF thereof.

As a result of intensive studies by the present inventors directed toward the above object, they have succeeded in determining the sequence of a canine HGF gene using the RT-PCR method, thereby completing the present invention.

That is to say, the present invention is a recombinant protein of the following (a) or (b):
(a) a protein having an amino acid sequence shown in SEQ ID NO: 2 or 4; and
(b) a protein having an amino acid sequence comprising a deletion, substitution or addition of one or several amino acids with respect to the amino acid sequence shown in SEQ ID NO: 2 or 4, and having a canine HGF activity.

In addition, the present invention is a gene encoding the following protein (a) or (b):
(a) a protein having an amino acid sequence shown in SEQ ID NO: 2 or 4; and
(b) a protein having an amino acid sequence comprising a deletion, substitution or addition of one or several amino acids with respect to the amino acid sequence shown in SEQ ID NO: 2 or 4, and having a canine HGF activity.

Moreover, the present invention is a gene comprising the DNA of the following (c) or (d):
(c) DNA comprising a nucleotide sequence shown in SEQ ID NO: 1 or 3; and
(d) DNA hybridizing with the DNA comprising the nucleotide sequence shown in SEQ ID NO: 1 or 3 under stringent conditions, and encoding a protein having a canine HGF activity.

Further, the present invention is a recombinant vector comprising one of the above-described genes.

Furthermore, the present invention is a transformant comprising the above-described recombinant vector.

Still further, the present invention is a method for producing a canine HGF, which is characterized in that it comprises culturing the above-described transformant and collecting a canine HGF from the obtained culture.

Still further, the present invention is a reagent for detecting a canine HGF which comprises at least a fragment of the above-described genes.

Still further, the present invention is a pharmaceutical composition comprising the above recombinant canine HGF, and the above-described pharmaceutical composition is used for the treatment of liver diseases, kidney diseases, lung diseases, bone diseases, digestive diseases, cardiocirculatory diseases or cranial nerve diseases.

This specification includes part or all of the contents as disclosed in the specification and/or drawings of Japanese Patent Application No. 2000-187724, which is a priority document of the present application.

THE BEST MODE FOR CARRYING OUT THE INVENTION

The present invention will be explained in detail below.

The present invention relates to a gene encoding a canine HGF (canine HGF; hereinafter, referred to as cHGF), which has a strong ability to regenerate impaired organs and is expected to be clinically applied to intractable organ diseases for which basic treatment methods have not yet been established; a recombinant cHGF; a recombinant vector comprising the gene; a transformant comprising the recombinant vector; a method of producing the cHGF; a method of detecting the cHGF; and a pharmaceutical composition comprising the cHGF. Moreover, the present invention relates to a variant cHGF (dcHGF), which lacks 15 base pairs in the first kringle domain corresponding to a receptor binding site, that is, a variant cHGF which lacks 5 amino acids, that is known to have a two or three times higher growth promoting activity on epithelium cells when compared with ordinary HGF and to have a different physiological action.

The present inventors extracted and purified RNA, and designed several primers, which are considered to be specific for HGF. Then, they carried out RT-PCR to obtain several DNA fragments. Some of the thus obtained DNA fragments were cloned in plasmid vectors to determine the nucleotide sequences. Based on the determined nucleotide sequences, overlapping portions of each DNA fragment were eliminated, and the sequence of a cHGF gene of interest was determined. Moreover, a 15 base pair-deleted cHGF generated by alternative splicing was isolated, and the sequence was determined. The sequences of the genes of the present invention were determined by this method.

1. Cloning of Gene of the Present Invention (1) Preparation of cDNA Clone by RT-PCR Examples of sources of mRNA include tissues such as the liver, the kidney, the lung, the brain, the thymus and the leukocyte of dog. Preparation of mRNA can be carried out by any conventional method. For example, the total RNA is extracted from the above-mentioned tissues or cells by the guanidium thocyanate-phenol method or the like, and poly (A)$^+$RNA(mRNA) is then obtained by the affinity column method or batch method, in which oligo dT-cellulose, poly U– sepharose or the like is used. Moreover, poly(A)$^+$RNA may further be fractioned by the sucrose density gradient centrifugation method.

Using the thus obtained mRNA as a template, a single strand cDNA is synthesized with oligo dT primers and reverse transcriptase. To obtain a clone comprising the DNA sequence of interest, for example, a degenerate sense primer and a degenerate antisense primer for the amino acid sequence of the already obtained HGF protein family are synthesized, PCR is carried out using these primers, and the obtained fragment is incorporated into a suitable cloning vector to prepare a recombinant vector. Using this recombinant vector, *Escherichia coli* or the like is transformed, and then, using tetracycline resistance or ampicillin resistance as an index, a transformant is selected so as to obtain a clone comprising a part or the full length of the sequences of cHGF and dcHGF genes Moreover, in the present invention, primers are not limited to the above-described primers.

Herein, transformation of *Escherichia coli* can be carried out by the Hanahan's method [Hanahan, D.: J. Mol. Biol. 166: 557–580 (1983)], which comprises adding a recombinant vector to a competent cell which is prepared by allowing calcium chloride, magnesium chloride or rubidium chloride to coexist. Where a plasmid is used as a vector, the plasmid should contain a drug resistance gene, which is resistant to tetracycline, ampicillin and so on. Moreover, a cloning vector other than a plasmid such as a ? phage (?gt11, etc.) can also be used.

(2) Determination of NUCLEOTIDE SEQUENCE of DNA Fragment

The nucleotide sequences of a single or multiple isolated clones comprising the above-described DNA fragment are determined, using a PCR product as a template. Determination of a nucleotide sequence can be carried out by any known methods such as the Maxam-Gilbert chemical modification method or the dideoxynucleotide chain termination method in which M13 phage is used, but in general, sequencing is carried out using an automatic nucleotide sequencer (e.g. a Model 310 fluorescent sequencer produced by Applied Biosystems). Based on nucleotide sequence information on a single or multiple DNA fragments derived from cHGF or a single or multiple DNA fragments derived from dcHGF, which are obtained by the above-described method, the nucleotide sequence of cHGF or dcHGF of interest is determined by eliminating overlapping portions.

The nucleotide sequence of the c HGF gene of the present invention is shown in SEQ ID NO: 1, the amino acid sequence of the cHGF of the present invention is shown in SEQ ID NO: 2, the nucleotide sequence of the 15 base pairs-deleted cHGF gene of the present invention is shown in SEQ ID NO: 3, and the amino acid sequence of the 5 amino acids-deleted cHGF of the present invention is shown in SEQ ID NO: 4. However, as long as a protein having this amino acid sequence exhibits a cHGF activity, the amino acid sequence may comprise a mutation such as a deletion, substitution or addition of at least one, preferably one or several amino acids.

For example, an amino acid sequence shown in SEQ ID NO: 2 or 4 may comprise a deletion of at least one, preferably one or several amino acids (for example, 1 to 10 amino acids, more preferably 1 to 5 amino acids). Or, an amino acid sequence shown in SEQ ID NO: 2 or 4 may comprise an addition of at least one, preferably one or several amino acids (for example, 1 to 10 amino acids, more preferably 1 to 5 amino acids). Otherwise, an amino acid sequence shown in SEQ ID NO: 2 or 4 may comprise a substitution of at least one, preferably one or several amino acids (for example, 1 to 10 amino acids, more preferably 1 to 5 amino acids) by other amino acids.

Moreover, the gene of the present invention also includes DNA hybridizing with the above gene under the following conditions and encoding a protein having a cHGF activity. That is to say, the conditions herein mean that, using a filter on which DNA is fixed, hybridization is carried out at 68° C. under 0.7 to 1.0 M NaCl followed by washing at 68° C. with 0.1 to 2×SSC solution (1×SSC consisting of 150 mM NaCl and 15 mM sodium citrate).

Furthermore, the present invention also includes RNA corresponding to the above DNA, or an RNA hybridizing with the RNA under stringent conditions and encoding a protein having a cHGF activity.

Introduction of a mutation into a gene can be carried out by any known technique such as the Kunkel method or the Gapped Duplex method, or an equivalent method. For example, the introduction of a mutation can be carried out, using a kit for introducing a mutation (e.g. Mutant-K (TAKARA), Mutant-G (TAKARA)), with which a site-directed mutagenesis is applied, or an LA PCR in vitro Mutagenesis series kit (TAKARA).

The gene of the present invention has a nucleotide sequence corresponding to the amino acid sequence of a cHGF, or the amino acid sequence of a 15 base pairs-deleted cHGF.

Once the nucleotide sequence of the gene of the present invention is determined, the gene of the present invention can then be obtained by chemical synthesis, by PCR in which cDNA is used as a template, or by performing hybridization, using a DNA fragment having the nucleotide sequence as a probe.

2. Preparation of Recombinant Vector and Transformant (1) Preparation of Recombinant Vector The recombinant vector of the present invention can be obtained by ligating (inserting) the gene of the present invention into a suitable vector. The vector into which the gene of the present invention is inserted is not to be particularly limited provided that it can replicate in a host, and examples of such a vector include plasmid DNA, phage DNA and others.

Examples of plasmid DNA include a plasmid derived from *Escherichia coli* (e.g. pBR322, pBR325, pUC118, pUC119, pUC18, pUC19, etc.), a plasmid derived from *Bacillus subtilis* (e.g. pUB110, pTP5, etc.), a plasmid derived from yeast (e.g. YEp13, YEp24, YCp50, etc.) and others. Examples of phage DNA include ? phage (Charon4A, Charon21A, EMBL3, EMBL4, ?gt10, ?gt11, ?ZAP, etc.). Moreover, an animal virus such as a retrovirus or vaccinia virus, or an insect virus vector such as a baculovirus, can also be used.

To insert the gene of the present invention into a vector, a method is applied, in which initially, purified DNA is cleaved with appropriate restriction enzymes, and the obtained DNA fragment is then inserted into the restriction site or the multicloning site of a suitable vector DNA to ligate the fragment to the vector.

It is necessary that the gene of the present invention is incorporated into a vector so that the functions of the gene are exhibited. Thus, not only can a promoter and the gene of the present invention, but also a cis-element such as an enhancer, a splicing signal, a poly(A) addition signal, a selective marker or a ribosome binding sequence (SD sequence), can be ligated to the vector of the present invention as desired. Examples of a selective marker include a dihydrofolate reductase gene, an ampicillin resistance gene, a neomycin resistance gene and others.

(2) Preparation of Transformant

The transformant of the present invention can be obtained by introducing the recombinant vector of the present invention into a host, so that the gene of interest can express therein. Herein, a host is not to be particularly limited provided that it allows the DNA of the present invention to be expressed. Examples of such a host include bacteria such as *Escherichia* sp. *Escherichia coli, Bacillus* sp. *Bacillus subtilis,* and *Pseudomonas* sp. *Pseudomonas putida;* yeast such as *Saccharomyces cerevisiae* and *Shizosaccharomyces pombe;* animal cells such as a COS cell and a CHO cell; and insect cells such as S121 and sf9. Moreover, an insect body itself from a silkworm, *Autographa california* or the like can also be used as a host.

Where a bacterium such as *Escherichia coli* is used as the host, it is preferable that the recombinant vector of the present invention be able to autonomously replicate in the bacterium and that the recombinant vector comprises a promoter, a ribosome binding sequence, the gene of the present invention and a transcription termination sequence. Moreover, a gene controlling the promoter may also be incorporated.

Examples of *Escherichia coli* include *Escherichia coli* DH1 and *Escherichia coli* JM109, and examples of *B. subtilis* include *Bacillus subtilis* and so on, but examples are not limited thereto.

Any promoter can be used provided that it can be expressed in a host such as *Escherichia coli.* For example, promoters derived from *Escherichia coli* or phage such as a trp promoter, a lac promoter, a $P_L$ promoter or a $P_R$ promoter can be used. An artificially designed and modified promoter such as a tac promoter may also be used.

A method for introducing a recombinant vector into a bacterium is not to be particularly limited provided that it is a method for introducing DNA into a bacterium. For example, a method of using calcium ion [Cohen, S. N. et al.: Proc. Natl. Acad. Sci., USA, 69: 2110(1972)], the electroporation method, etc. can be used.

Where yeast is used as the host, for example, *Saccharomyces cerevisiae, Schizosaccharomyces pombe* or *Pichia pastoris* is used. In the use of yeast as a host, any promoter can be used to such an extent that it can be expressed in yeast, and examples of such a promoter include a gall promoter, a gal10 promoter, a heat shock protein promoter, an MFa1 promoter, a PH05 promoter, a PGK promoter, a GAP promoter, an ADH promoter, an AOX1 promoter and others.

A method for introducing a recombinant vector into yeast is not particularly to be limited provided that it is a method for introducing DNA into yeast, and examples of such a method include the electroporation method [Becker, D. M. et al.: Methods. Enzymol., 194: 182 (1990)], the spheroplast method [Hinnen, A et al.: Proc. Natl. Acad. Sci., USA, 75: 1929 (1978)], the lithium acetate method [Itoh, H.: J. Bacteriol., 153: 163 (1983)] and others.

Where an animal cell is used as the host, a monkey cell COS-1 or COS-7, Vero, a Chinese hamster ovary cell (CHO cell), a mouse L cell, a rat GH3, a human FL cell, etc. can be used. Examples of promoters used include an SRa promoter, an SV40 promoter, an LTR promoter, a CMV promoter and others, and further a human cytomegalovirus immediate early gene promoter or the like may also be used. Examples of methods of introducing a recombinant vector into an animal cell include the electroporation method, the calcium phosphate method, the lipofection method and others.

Where an insect cell is used as a host, an S121 cell, an Sf9 cell, etc. can be used. Examples of a method of introducing a recombinant vector into an insect cell include the calcium phosphate method, the lipofection method, the electroporation method, etc.

Further, where an insect body itself is used, a silkworm, *Autographa california* and so on can be used. A method of introducing a recombinant virus into an insect body includes natural infection.

(3) Production of Protein of the Present Invention

The protein of the present invention is a protein having an amino acid sequence encoded by the cHGF gene or the 15 base pairs-deleted cHGF gene of the present invention, or a protein having an amino acid sequence comprising the above-described mutation introduced into at least one amino acid relative to the above amino acid sequence and having a cHGF activity. It should be noted that the protein of the present invention is also referred to as a cHGF protein, and a 15 base pairs-deleted type thereof is also referred to as a 5 amino acids-deleted cHGF protein.

The cHGF protein of the present invention can be obtained by culturing the above-described transformant and collecting the cHGF from the cultured product. The term a "cultured product" is herein used to mean any of a culture supernatant, a cultured cell or cultured cell body, and a homogenized product of the cell or cell body.

The culture of the transformant of the present invention is carried out according to common methods used for the culture of a host.

As a medium for culturing a transformant obtained while using a microorganism such as *Escherichia coli* or yeast as a host, either a natural medium or a synthesized medium can be used to such an extent that the medium contains a carbon source, a nitrogen source, inorganic salts and others, which can be assimilated by the microorganism, and can be efficiently utilized in the culture of the transformant.

Examples of a carbon source include carbohydrates such as glucose, fructose, sucrose or starch, organic acids such as acetic acid or propionic acid, and alcohols such as ethanol and propanol.

Examples of a nitrogen source include an inorganic or organic ammonium salt such as ammonia, ammonium chloride, ammonium sulfate, ammonium acetate or ammonium phosphate, other nitrogen-containing compounds, peptone, meat extract, corn steep liquor and others.

Examples of an inorganic product include potassium primary phosphate, potassium secondary phosphate, magnesium phosphate, magnesium sulfate, sodium chloride, ferrous sulfate, manganese sulfate, copper sulfate, calcium carbonate and others.

Generally, culture is carried out at 37° C. under aerobic conditions such as shaking culture or aeration and agitation culture. Control of the pH of the medium is carried out using an inorganic or organic acid, or an alkaline solution.

During culture, an antibiotic such as ampicillin or tetracycline may be added to the medium as necessary.

For culturing a microorganism transformed with an expression vector comprising an inducible promoter, an inducer may be added to the medium as necessary. For example, when a microorganism transformed with an expression vector comprising a Lac promoter is cultured, isopropyl-β-D-thiogalactopyranoside (IPTG) or the like may be added to the medium, and when a microorganism transformed with an expression vector comprising a trp promoter, indoleacetic acid (IAA) or the like may be added thereto.

For culturing a transformant obtained by using an animal cell as a host, commonly used RPMI 1640 medium, DMEM medium or a medium obtained by adding fetal bovine serum or the like to these media, can be used.

Generally, culture is carried out at 37° C. for 1 to 30 days in the presence of 5% $CO_2$. During culture, an antibiotic such as kanamycin or penicillin may be added to the medium as necessary.

Where the protein of the present invention is produced inside a cell body or cell after culture, a cHGF protein is extracted by homogenizing the cell body or the cell. Where the protein of the present invention is produced outside a cell body or cell, the culture solution is used as is, or the cell body or the cell is eliminated by centrifugal separation or the like. After that, the protein of the present invention can be isolated and purified from the above culture by biochemical methods commonly used for isolation and purification of proteins, used either singly or in combination, e.g. ammonium sulfate precipitation, gel chromatography, ion exchange chromatography, affinity chromatography and others.

3. Method of Detecting cHGF Using the Gene of the Present Invention and Detection Reagent (1) Use of the Gene of the Present Invention or Portion Thereof as Probe In the present invention, a probe hybridizing with the above-described DNA or RNA and specifically detecting the DNA or the RNA is also provided as a reagent for detecting a cHGF. This probe is labeled with a commonly used radioisotope (e.g. $^{32}P$, $^{35}S$), an enzyme (e.g. digoxigenin, fluororescein) or the like, and the labeled probe is then hybridized specifically with the DNA or the RNA by a common blotting analysis, In situ hybridization or the like, thereby detecting the DNA or the RNA.

DNA or RNA used as a probe in the present invention has at least a portion of the nucleotide sequence of the DNA or the RNA which are shown in SEQ ID NO: 2 or 3 and SEQ ID NO: 5 or 6. The length of the probe is 200 to 300 nucleotides, but it may have an entire sequence and it is not particularly limited.

4. Pharmaceutical Composition Comprising the Recombinant cHGF of the Present Invention The recombinant cHGF or the 15 base pairs-deleted HGF thereof of the present invention is a recombinant cHGF or a 5 amino acids-deleted HGF thereof, which has been extracted and purified, or a recombinant cHGF or a 5 amino acids-deleted HGF thereof, which has been inserted into a plasmid or the like and allowed to translate inside the body of a dog. Such a factor is used as a pharmaceutical composition for the treatment of liver diseases such as fulminant hepatitis, acute hepatitis, hepatocirrhosis, lung fibrosis, fatty liver and liver cancer, kidney diseases such as acute renal failure, chronic renal failure/nephrosclerosis, renal transplantation and diabetic nephropathy, lung diseases such as acute pneumonia and liver fibrosis, bone diseases such as osteoarthritis deformans and arthritis rheumatica, digestive diseases such as gastric ulcer and diabetes (suppression of apoptosis of β cells of pancreas, promotion of insulin production), cardiovascular diseases such as myocardial infarction, hypertrophic/congestive cardiomyopathy and angiopathy (diabetic retinopathy, arteriosclerosis obliterans, etc.), and cranial nerve diseases such as cerebral infarction and Parkinson's disease.

The pharmaceutical composition of the present invention is particularly useful for the treatment of chronic canine diseases such as canine chronic renal failure, and this composition has no antigenic side effects and can be used for a long time.

The pharmaceutical composition of the present invention comprises a cHGF or a 15 base pairs-deleted HGF thereof or a salt thereof or a DNA fragment of a cHGF gene or dcHGF gene bound to a plasmid or the like to be translates inside the body of a dog with a pharmacologically acceptable carrier, diluent or excipient. The pharmaceutical composition of the present invention can be administered in various forms. Examples of such an administration form include orally administration using tablets, capsules, granules, powders or syrups, or parenterall administration using injection, drop or suppository. Such a composition is produced by any known method and comprises a carrier, a diluent and an excipient, which are commonly used in the pharmaceutical field. For example, as a carrier or excipient used for a tablet, lactose, magnesium stearate or the like is used. An injection is prepared by dissolving, suspending or emulsifying the cHGF or a salt thereof in a sterile aqueous or oily solution. Examples of aqueous solution used for an injection include a physiological salt solution and an isotonic solution containing glucose or another adjuvant, and the aqueous solution may be used in combination with an appropriate solution adjuvant such as alcohol, polyalcohol such as propylene glycol or a nonionic surfactant. Examples of the above-mentioned oily solution include sesame oil, soybean oil and so on, and the oily solution may be used in combination with a solution adjuvant such as benzyl benzoate or benzyl alcohol.

The dosage applied depends on symptom, age, body weight and others. In the case of oral administration, generally, it is approximately 0.001 mg to 1,000 mg per dog per day, and the pharmaceutical composition with the above dosage is administered all at once, or divided several times throughout a day. In contrast, in the case of parenteral administration, 0.001 mg to 1,000 mg of the pharmaceutical composition is administered per dog per day in the form of a subcutaneous injection, intramuscular injection or intravenous injection. Moreover, in the case of using a recombinant cHGF or recombinant dcHGF inserted into a plasmid and allowed to translate inside the body of a dog, 0.001 mg to 1,000 mg is administered per dog every several days, weeks or months in the form of a subcutaneous, intramuscular or intravenous injection.

BRIEF DISCRIPTION OF THE DRAWINGS

EXAMPLES

Figure 1:
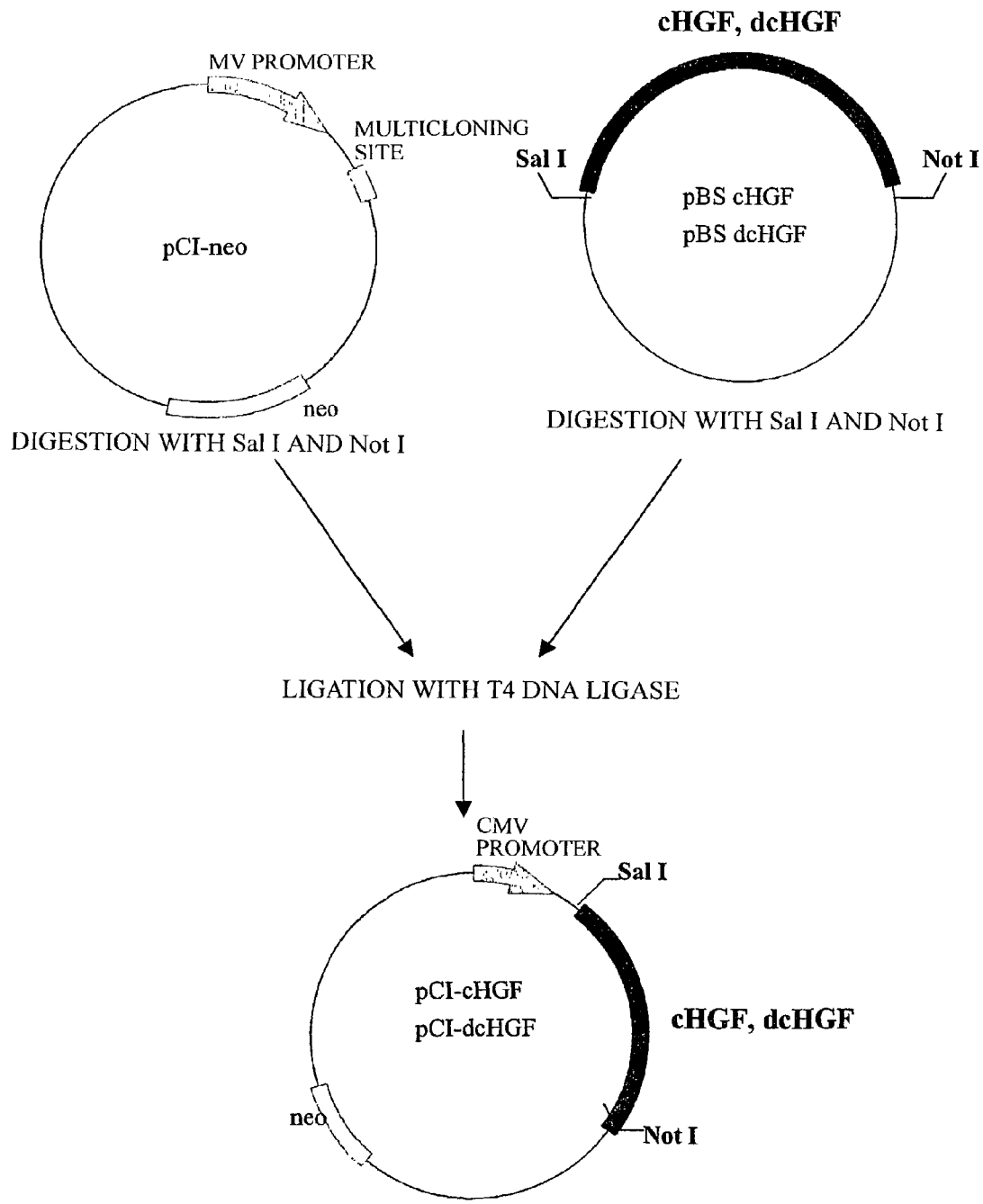
FIG. 1 shows the construction of recombinant cHGF and dcHGF vectors for the expression of a protein, which are used in COS-1 cells and CHO cells in Example 2.

The present invention is further specifically described in the following examples. The examples are provided for illustrative purposes only, and are not intended to limit the technical scope of the invention.

Example 1

Isolation of cHGF Gene (a) Obtainment of DNA Fragment Derived from cHGF

To clone the full length of a cHGF protein translated region, initially, primers were designed on the basis of a nucleotide sequence corresponding to the 5' and 3' protein untranslated regions of a hHGF gene that had already been reported, and then amplification by the RT-PCR method was attempted. However, it was difficult to obtain an amplified product having the desired size. Thus, primers were instead designed, using a nucleotide sequence as an index, that is relatively well conserved over animal species such as human, mouse and rat. Thereafter, a cHGF cDNA partial sequence was cloned by the RT-PCR method, and uncloned regions located at 5' and 3' sides were then cloned by 5' and 3' RACE (rapid amplification of cDNA ends) method.

Cloning of a partial sequence of cHGF: The total RNA was extracted from a canine leukocyte by the guanidium thio-cyanate-phenol method (Trizol Reagent (Gibco-BRL). Using 3' RACE System (Gibco-BRL), cDNA was synthesized from the extracted total RNA and was then subjected to an RT-PCR reaction.

Using an already reported nucleotide sequence as an index that is relatively well conserved over animal species such as human, mouse and rat, primers were designed in an HGF gene protein translated region. A reaction solution having a composition set forth below was used for the PCR reaction. After a reaction was carried out at 94° C. for 2 minutes, the following cycle was repeated 30 times: 94° C. for 1 minute, 55° C. for 1 minute and 72° C. for 2 minutes. Finally, a reaction was carried out at 72° C. for 5 minutes. Thereafter the temperature of the reacted solution was maintained at 4° C.

Composition of reaction solution: 1×PCR buffer, 0.2 mM dNTP, 0.005 units/μl Taq polymerase (TaKaRa EX Taq), 0.5 μM each of the following primers:

```
Sense primer:
5' CCATGAATTTGACCTCTATG 3'              (SEQ ID NO: 5)

Antisense primer:
5' TGTGTATCCATTTTGCATAATATGCTACTC 3' (SEQ ID NO: 6)
```

The obtained PCR product was subjected to agarose gel electrophoresis in the presence of ethidium bromide to confirm the size of the product. Products having measurable sizes were purified from the agarose gel (RECOCHIP (TaKaRa)), and ligated to the cloning site of a plasmid vector using T4DNA ligase (pGEM-T Easy Vector System (Promega)) so as to transform the host *Escherichia coli* JM109 (Promega). That is to say, after the *Escherichia coli* competent cell was mixed with the plasmid, the mixture was subjected to a temperature treatment on ice for 30 minutes, at 42° C. for 45 seconds, and on ice for 5 minutes. Then, the mixture was suspended in a High-competence broth (Nippon Gene Co., Ltd.) for incubation at 37° C. for 1 hour. Thereafter, it was placed on LB agar medium to which 50 µg/ml ampicillin was added, so that a transformed *Escherichia coli* colony was obtained. The transformed *Escherichia coli* was cultured at 37° C. overnight on LB medium (1% yeast extract, 0.5% tripton, 1% NaCl) to which 50 µg/ml ampicillin was added. After that, plasmid DNA was purified (ultraclean mini plasmid DNA purification kit, MO BIO), and the nucleotide sequence was determined (Espec Oligo Service Corp., ABI 310 DNA sequencer). Homology search was performed on the obtained nucleotide sequence, using an online homology search program, BLAST. Because the obtained nucleotide sequence showed high homology with the HGF gene of human or other animal species, it is suggested that this sequence was a partial sequence of a cHGF gene.

Cloning of 3' untranslated region by 3' RACE method: Primers were designed on the basis of the nucleotide sequence of the obtained cHGF partial sequence, and 3' RACE was carried out using SMART RACE cDNA Amplification Kit (Clontech). Agarose gel electrophoresis and ethidium bromide staining were carried out on the first PCR product. However, since no amplified fragments were observed, nested PCR was carried out and an amplified fragment was obtained by 3' RACE.

The composition of the PCR reaction solution was prepared according to the manufacturer's instructions. A PCR cycle at 94° C. for 5 seconds, at 68° C. for 10 seconds and at 72° C. for 3 minutes was repeated 25 times.

1st primer:
5' ATGCAGCCAATACCATCAAGGGAAGGTGAC 3' (SEQ ID NO: 7)

Nested primer:
5' TCAGGACCATGTGAGGGAGATTATGGTGGC 3' (SEQ ID NO: 8)

The length of the obtained amplified product was approximately 1.7 kbp, and it was different from about 3.6 kbp, which was the length of 3' protein untranslated region estimated from the cDNA of the already reported human and rat HGF. However, from the analysis of the nucleotide sequence, it was found that this amplified fragment comprised a termination codon, poly A signal and poly A sequence, and so it was suggested that this was a variant generated by alternative splicing in the 3' protein untranslated region.

Cloning of 5' untranslated region by 5' RACE method: Primers were designed on the basis of the nucleotide sequence of the obtained cHGF partial sequence, and 5' RACE was carried out using SMART RACE cDNA Amplification Kit (Clontech) so as to attempt the cloning of the 5' untranslated region.

The 5' RACE was carried out using a reaction solution and a PCR cycle set forth below. Agarose gel electrophoresis and ethidium bromide staining were carried out on the first PCR product. However, since no amplified fragments were observed, nested PCR was carried out and an amplified fragment was obtained by 5' RACE.

1st primer:
                                (SEQ ID NO: 9)
5' CTTCGTAGCGTACCTCTGGATTGCTTGTG 3'

Nested primer:
                                (SEQ ID NO: 10)
5' TTCCAGGGCTGGCATTTGATGCCACTC 3'

The composition of the PCR reaction solution was prepared according to the manufacturer's instructions. A PCR cycle at 94° C. for 5 seconds, at 68° C. for 10 seconds and at 72° C. for 2 minutes was repeated 25 times. After agarose gel electrophoresis and ethidium bromide staining were performed on the nested PCR product, a multiple number of bands were observed. The longest amplified fragment was purified from the agarose gel by the same method as described above, and the fragment was cloned into a pGEM-T Easy vector followed by analysis of the nucleotide sequence. However, an initiation site for protein translation did not comprise the obtained amplified fragment.

Since the full length of an HGF gene is about 6 kbp and is a relatively large gene, it is technically difficult to clone the sequence of the 5' end. Considering that the nucleotide sequence of the mRNA of cHGF is expected to have a conformation for which normal reverse transcription reaction can hardly be carried out, therefore it was extremely difficult to obtain a full length cDNA. In fact, to clone the translation initiation point of the cHGF gene, a total of 6 types of cDNA synthesis for 5' RACE was carried out, including: SMART RACE cDNA Amplification Kit (Clontech) and 3 types of reverse transcriptase, Superscript II (Gibco-BRL), Powerscript II (Clontech), and subsequent application of M-MLV Reverse Transcriptase RNase Minus (Promega). Moreover, for the PCR reaction, 9 types of primers were designed on the basis of the above described cHGF partial sequence and the nucleotide sequence of the cHGF gene which was determined by the first 5' RACE. Then, a nested PCR reaction, the cloning of the amplified product and the analysis of the nucleotide sequence were carried out with a large number of combinations. While it was extremely difficult to obtain a clone comprising a translation initiation point, as a result of continuous efforts, however, using cDNA synthesized with M-MLV Reverse Transcriptase RNase Minus (Promega), PCR reaction was performed with the following combination of primers:

1st primer:
5' GGCCTTGCAAGTGAATGGAAGTCC 3'      (SEQ ID NO: 11)

Nested primer:
5' ACGGCGACGGGCAGCAGGAGGAGGTGC 3', (SEQ ID NO: 12)

thereby obtaining an amplified product, which is predicted to comprise a translation initiation point.

The composition of the reaction solution and the conditions for PCR cycle were the same as for the first 5' RACE. The obtained PCR products were not single amplification products, but the products were purified from the agarose gel by the same method as stated above and were then cloned into a pGEM-T Easy vector. Thereafter, 24 clones were randomly selected, and as a result of analysis of each nucleotide sequence, it was found that 3 clones each thereof comprised a translation initiation point.

(b) Analysis of Nucleotide Sequence of Inserted Fragment

The nucleotide sequences of the gene fragments obtained in (a) were combined using Genetyx-win ver. 4 software (Software Development) to obtain the entire nucleotide sequence of the cHGF gene protein translated region. The sequence is shown in SEQ ID NO: 1. This sequence consists of 2,193 bp. Using GENBANK/EMBL DNA Data Base, research was made for the nucleotide sequence shown in SED ID NO: 1. However, an identical sequence was not present. Accordingly, it was confirmed that DNA having this nucleotide sequence was an entirely new DNA. When homology searching was carried out using an online homology search program, BLAST and Genetyx-win ver. 4 software, the nucleotide sequence of SEQ ID NO: 1 showed high homology with the nucleotide sequences of the HGF genes of human (92.2%), mouse (87.8%) and rat (87.5%).

The amino acid sequence predicted from the nucleotide sequence of SEQ ID NO: 1 is shown in SEQ ID NO: 2. When the amino acid sequence was subjected to homology analysis as in the case with the nucleotide sequence, the amino acid sequence of SEQ ID NO: 2 showed high homology with the amino acid sequences of the HGFs of human (92.3%), mouse (92.1%) and rat (92.0%). From these results, it was strongly suggested that the nucleotide sequence of SEQ ID NO: 1 is a cHGF gene.

(c) Amplification of Full Length cHGF Protein Translated Region

Primers were designed based on the nucleotide sequence obtained in (a) so as to amplify the cHGF protein translated region, and PCR was carried out using, as a template, cDNA derived from canine leukocyte. A reaction solution having a composition set forth below was used for the PCR reaction. After reaction was carried out at 94° C. for 2 minutes, the following reaction cycle was repeated 30 times: at 94° C. for 30 seconds, at 55° C. for 30 seconds and at 68° C. for 2 minutes. Finally, a reaction was carried out at 68° C. for 5 minutes, and the reaction solution temperature was maintained at 4° C.

Composition of reaction solution: 1×PCR buffer, 1 mM MgSO$_4$, 0.2 mM dNTP, 0.005 units/µl Taq polymerase KOD Plus (Toyobo), 0.5 µM each of the following primers:

```
Sense primer:
5' ATGTGGGTGACCAAGCTCC 3'           (SEQ ID NO: 13)

Antisense primer:
5' TGGGTGCTTCAGACACACTTACATCAG 3'   (SEQ ID NO: 14)

Nested sense primer:
5' ATGTGGGTGACCAAGCTCCTGCCCCTG 3'   (SEQ ID NO: 15)

Nested antisense primer:
5' CTATGACTGTTGTATCTTATACGTTAA 3'   (SEQ ID NO: 16)
```

The obtained PCR product was subjected to agarose gel electrophoresis in the presence of ethidium bromide to confirm the size of the product. Then, the product was cloned into a plasmid vector by the same method as described above, and the nucleotide sequence was analyzed. From the results of analysis, one clone wherein the 414$^{th}$ nucleotide, from the translation initiation point, was adenine, and another clone wherein the 414$^{th}$ nucleotide was guanine, were found. A multiple number of clones were obtained for both adenine and guanine, and it is considered that this occurrence is due to a single nucleotide polymorphism. Nevertheless, the amino acid encoded by these two clones was glycine, and no difference was observed in the amino acid sequences. Other sequences completely matched those obtained in (a).

(d) Screening of 15 Base Pairs-deleted cHGF

When the nucleotide sequence of the cHGF partial sequence described in (a) was analyzed, in one of the three analyzed clones, it was found that 15 base pairs at a site corresponding to the first kringle domain were deleted due to alternative splicing. The same alternative splicing had also been reported regarding human, rat and mouse, but this is the first research showing that alternative splicing caused the deletion of 15 base pairs in the first kringle domain in a cHGF gene. To screen for this 15 base pairs-deleted cHGF (hereinafter, dcHGF), primers were designed so that the primers sandwich the deleted site. Then, using, as a template, an *Escherichia coli* colony transformed with vector DNA to which the full length protein translated region of a cHGF gene described in (c) was ligated, PCR was carried out using a reaction solution having a composition set forth below. After a reaction was carried out at 94° C. for 2 minutes, the following reaction cycle was repeated 30 times: at 94° C. for 30 seconds, at 55° C. for 30 seconds and at 72° C. for 30 seconds. Finally, a reaction was carried out at 72° C. for 5 minutes followed by maintaining the temperature at 4° C.

Composition of reaction solution: 1×PCR buffer, 0.2 mM dNTP, 0.005 units/µl Taq polymerase (TaKaRa EX Taq), 0.5 µM each of the following primers:

```
Sense primer:
5' CTATCACTAAGAGTGGCATC 3'     (SEQ ID NO: 17)

Antisense primer:
5' GGAATGTCACAGACTTCGTAG 3'    (SEQ ID NO: 18)
```

The obtained PCR product was subjected to 4% agarose gel electrophoresis in the presence of ethidium bromide, and comparisons were made regarding the lengths of the amplified fragments of each clone. A clone having an amplified fragment shorter than a common fragment was selected. After the clone was cultured in LB medium overnight as stated above, plasmid DNA was purified and the nucleotide sequence was analyzed. The sequence is shown in SEQ ID NO: 3. The amino acid sequence predicted from the nucleotide sequence of SEQ ID NO: 3 is shown in SEQ ID NO: 4. The obtained dcHGF clone lacked 15 base pairs at a site corresponding to the first kringle domain, and as a result, 5 amino acids are missing. Further, as described in (c) above, even in 15 base pairs-deleted dcHGF, there existed both one clone wherein the 414$^{th}$ nucleotide, from the translation initiation point, was adenine and another clone wherein the 414$^{th}$ nucleotide was guanine. No differences were found for other nucleotide and amino acid sequences.

Example 2

Production of Recombinant cHGF Protein and Recombinant dcHGF Protein Using Mammalian Cell (a) Production of Recombinant Plasmid for Expression in Mammalian Cell Comprising DNA Encoding cHGF and dcHGF A one µg sample of the plasmid obtained in Example 1 (c) and (d) was digested with 10 units of restriction enzymes Sal I and Not I (TaKaRa) at 37° C. for 2 hours, and then subjected to agarose gel electrophoresis. Approximately 2.2 kbp DNA fragments of cHGF and dcHGF were purified using RECOCHIP (TaKaRa). On the other hand, 1 μg of an expression vector for mammalian cells, pCI-neo Mammalian Expression Vector (Promega), was digested with 10 units of restriction enzymes Sal I and Not I (TaKaRa) at 37° C. for 2 hours, and then subjected to phenol chloroform treatment and ethanol precipitation according to a common technique so that the final concentration was maintained at 50 ng/μl. The above cHGF and dcHGF DNA fragments were ligated to an expression vector DNA of ligation kit ver. 2 (TaKaRa), and *Escherichia coli* was transformed by the above-described method. An *Escherichia coli* clone comprising cHGF and dcHGF genes was selected and plasmid DNA was purified (FIG. 1). Using an expression vector-derived sequence primer, T7-EEV (Promega), analysis of the nucleotide sequence was carried out and it was confirmed that the DNA fragments of cHGF and dcHGF were ligated as designed.

(b) Production of Recombinant cHGF and dcHGF Proteins in COS-1 Cells

Figure 2:
FIG. 2 shows the biological activity of cHGF and dcHGF produced in COS-1 cells in Example 2.
Figure 2:
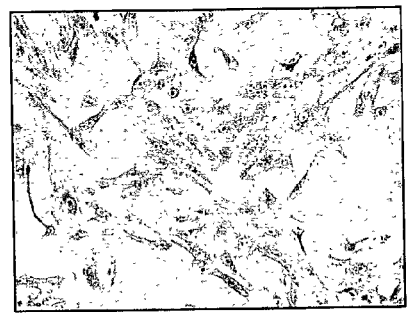
Figure 2:
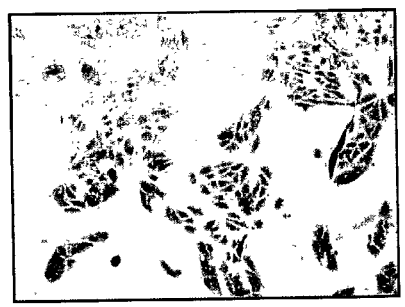

African green monkey COS-1 cells were maintained in E-MEM medium (Nissui Pharmaceutical Co., Ltd.) containing 10% fetal bovine serum (Moregate) and 0.3% Tryptose Phosphate broth (DIFCO) at 37° C. in the presence of 5% $CO_2$. A day before transformation, the COS-1 cells, which were proliferated to a confluent condition, were washed with PBS buffer, and then a trypsin-EDTA solution was added thereto and the mixture was left statically at room temperature for about 2 minutes. After the above medium was added thereto and the cells were well suspended, centrifugation was carried out at 1,200 rpm at 4° C. for 5 minutes. After the supernatant was eliminated, the remaining solution was suspended again in the medium, and the number of cells was counted according to a common technique. The number of cells was adjusted so that $8\times10^5$ cells were present in 5 ml of medium, and the cells were placed in a 60 mm-diameter petri dish (FALCON) and cultured at 37° C. overnight in the presence of 5% $CO_2$. The plasmid DNA for the expression of cHGF and dcHGF obtained in (a) was purified (Wizard SV Minipreps DNA purification system (Promega)) and adjusted so that the concentration was 1 μg/μl in distilled water. The introduction of the gene into the COS-1 cells were carried out using Lipofectamine 2000 Regent (GIBCO-BRL), and the gene transfer was carried out according to the manufacturer's instructions. After the transfectionof the gene, culture was carried out at 37° C. for 48 hours in the presence of 5% $CO_2$, so as to obtain the culture supernatant in which recombinant cHGF and dcHGF were produced. This culture supernatant was collected and the biological activity was determined in the manner described in Example 4. The enhanced cell mobility in MDCK cell was observed, and so it was confirmed that the recombinant cHGF and dcHGF proteins produced in COS-1 cells exhibited a biological activity (FIG. 2).

Figure 3:
FIG. 3 shows the biological activity of cHGF and dcHGF produced in CHO cells in Example 2.
Figure 3:
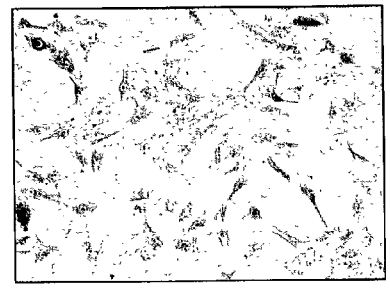
Figure 3:
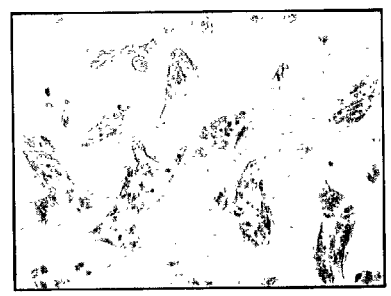

(c) Production of Cell Line which Stably Expresses the Recombinant cHGF and dcHGF Proteins Using a Chinese hamster CHO cells, a cell line which stably expresses the recombinant cHGF and dcHGF proteins were obtained. This CHO cells were maintained in E-MEM medium (Nissui Pharmaceutical Co., Ltd.) containing 10% fetal bovine serum (Moregate) and 0.3% Tryptose Phosphate broth (DIFCO) at 37° C. in the presence of 5% $CO_2$. A day before transformation, the CHO cells, which were proliferated to a confluent condition, were removed from the plate and resuspended in the medium by the above-described method, and the number of cells was counted. The number of cells was adjusted so that $1.2\times10^5$ cells were present in 500 μl of medium, and the cells were placed in a 24-well petri dish (FALCON) and cultured at 37° C. overnight in the presence of 5% $CO_2$. The plasmid DNA for expression of cHGF and dcHGF obtained in (a) was purified (Wizard SV Minipreps DNA purification system (Promega)) and adjusted so that the concentration was 1 μg/μl in distilled water. The transfection of the gene into CHO cells were carried out using Lipofectamine 2000 Regent (GIBCO-BRL), and the gene transfer operation was carried out according to the manufacturer's instructions. After the introduction of the gene, culture was carried out at 37° C. overnight in the presence of 5% $CO_2$. Thereafter, cells were harvested by the above-described method and resuspended in 12 ml of the above-described medium containing 600 μg/ml of GENETICIN (GIBCO BRL). A total of 500 μl of the suspension was poured into a 24-well Petri dish (FALCON), and cultured at 37° C. in the presence of 5% $CO_2$. The medium was replaced by a new medium approximately every 3 days, and culture was continuously carried out for about 2 weeks to obtain stable expression cell lines. The cell lines were screened from the culture supernatant by a limiting dilution analysis, so as to obtain cell lines with high recombinant cHGF and dcHGF protein producing activities. The obtained high production cell lines were cultured in the above medium at 37° C. for several days in the presence of 5% $CO_2$, so as to obtain the culture supernatant in which recombinant cHGF and dcHGF proteins were produced. When this culture supernatant was collected and the biological activity was determined in the manner described in Example 4, enhanced cell mobility in MDCK cell was observed. Thus, it was confirmed that the recombinant cHGF and dcHGF proteins produced in CHO cells exhibited a biological activity (FIG. 3).

Example 3

Figure 4:
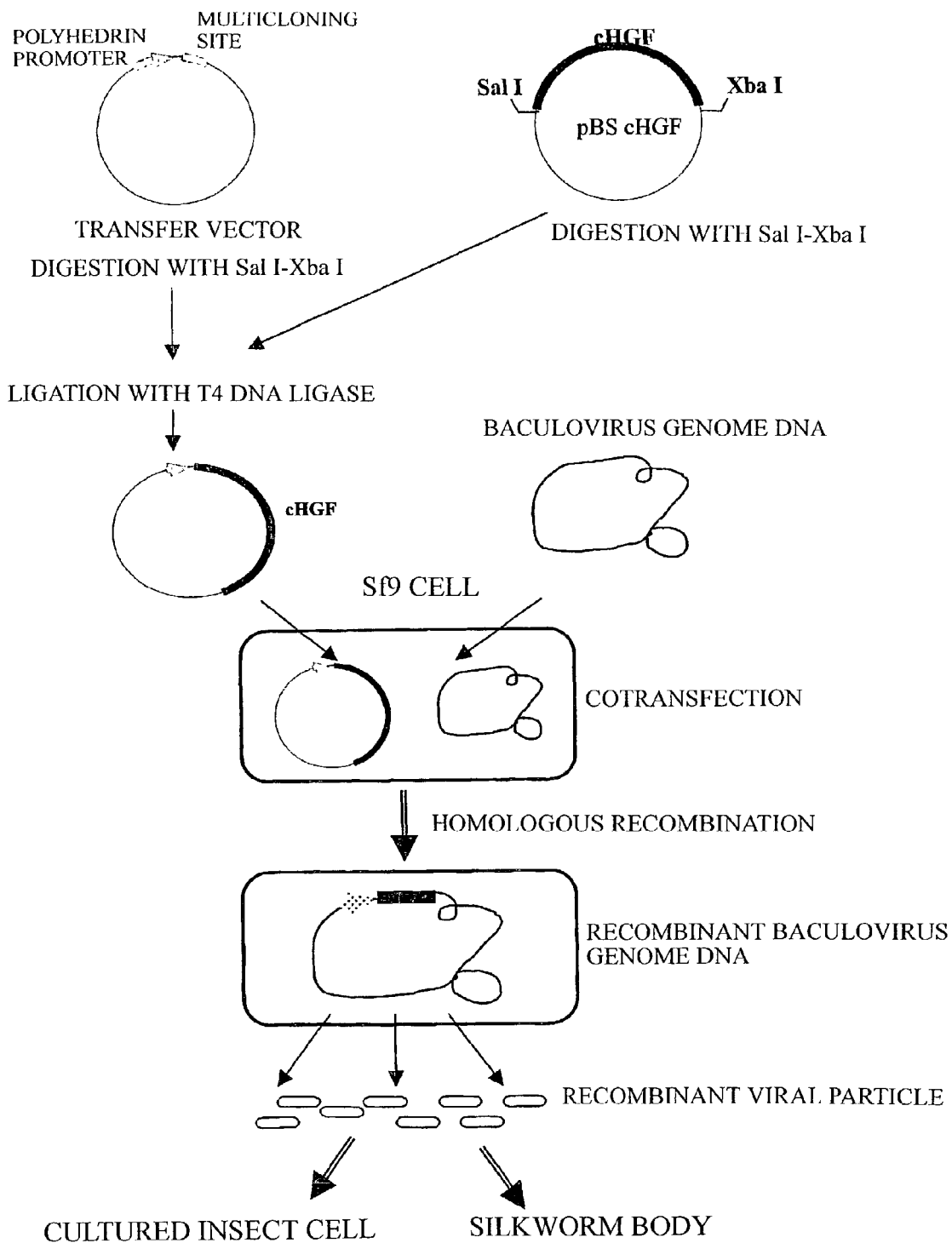
FIG. 4 shows the construction of a recombinant cHGF virus vector, for expression of a protein, which has been introduced into silkworm larvae and cultured insect cells in Example 3.
Figure 5:
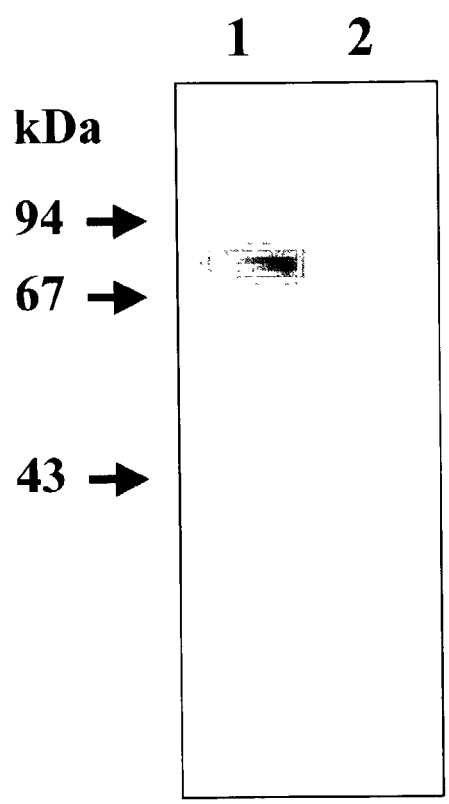
FIG. 5 shows the result of Western Blotting analysis of a recombinant cHGF produced in the silkworm larvae of Example 3. Lane 1 shows the results obtained from the haemolymph of a silkworm infected with a cHGF recombinant virus, and lane 2 shows the results obtained from the haemolymph of silkworm larvae infected with a non-recombinant virus.
Figure 6:
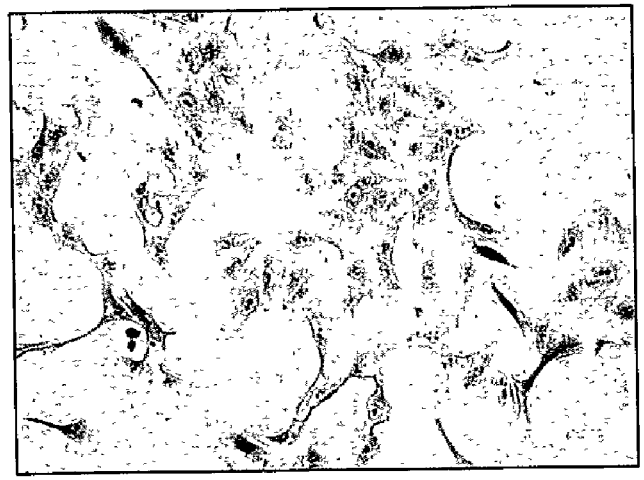
FIG. 6 shows the biological activity of a recombinant cHGF protein, which was produced in the silkworm larvae of Example 3.
Figure 6:

Production of Recombinant cHGF Protein in Silkworm Larvae and Cultured Insect Cells (a) Production of Recombinant cHGF Protein in Silkworm Larvae By using the Superworm Service of Katakura Industries Co., Ltd., a recombinant baculovirus transformed with DNA encoding cHGF was obtained using the plasmid vector obtained in Example 1 (c) (FIG. 4). The viral liquid of the obtained recombinant virus was inoculated into silkworm larvae, and after breeding for several days, the haemolymph was collected from the silkworm larvae. According to a common technique, the haemolymph sample was subjected to SDS-polyacrylamide electrophoresis, and then to Western Blotting analysis so as to detect the recombinant cHGF protein at the position of a molecular weight of about 80,000 to 90,000 (FIG. 5). Further, when the biological activity was determined in the manner described in Example 4, enhanced cell mobility in MDCK cell was observed. Thus, it was confirmed that the recombinant cHGF protein produced in the silkworm larvae exhibited a biological activity (FIG. 6).

(b) Production of Recombinant cHGF Protein in Cultured Insect Cells

Figure 7:
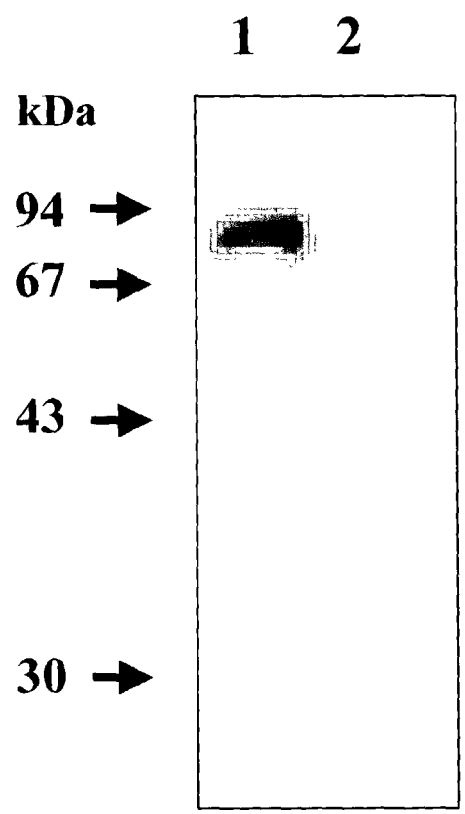
FIG. 7 shows the results of Western Blotting analysis of a recombinant cHGF, which is produced in the cultured insect cells of Example 3. Lane 1 shows the results obtained from the culture supernatant of Sf9 cells infected with a cHGF recombinant virus, and lane 2 shows the results obtained from the culture supernatant of Sf9 cells infected with a non-recombinant virus.
Figure 8:
FIG. 8 shows the biological activity of a cHGF protein produced in the cultured insect cells of Example 3.
Figure 8:
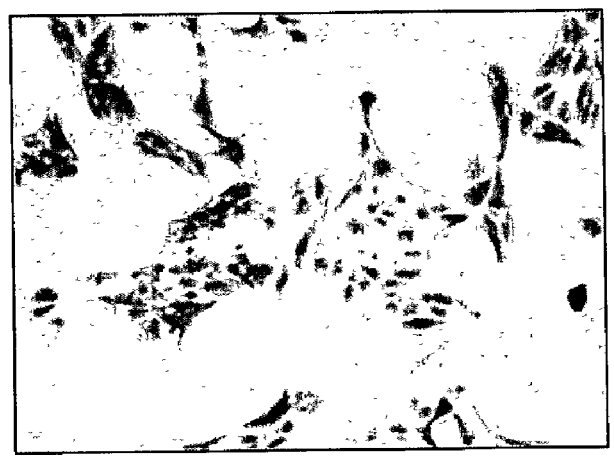

The above-obtained recombinant viral liquid was added to an Sf9 cell culture supernatant, and after culture for approximately 1 week, the culture supernatant was collected. The culture supernatant sample was subjected to SDS-polyacrylamide electrophoresis according to a common technique and then to Western Blotting analysis so as to detect the recombinant cHGF protein at the position of a molecular weight of about 80,000 to 90,000 (FIG. 7). Further, when the biological activity was determined in the manner described in Example 4, enhanced cell motility in MDCK cell was observed. Thus, it was confirmed that the recombinant cHGF protein produced in the cultured insect cells exhibited a biological activity (FIG. 8).

Example 4

Determination of Biological Activity of Recombinant cHGF and dcHGF Proteins

The biological activity of recombinant cHGF and dcHGF proteins were determined by observing for enhancement of cell motility in Madin-Darby Canine Kidney (MDCK) cells. The MDCK cells were maintained in the above expansion medium. The cells which proliferated to the confluent conditonwere harvested from the plate by the above-described method, and the number of cells was counted and then the cells were adjusted so that the number of the cells was $3 \times 10^4$ cells/ml. From this obtained cell suspension, 100 μl was dividely poured into each well of a 96-well plate (FALCON). Then, 50 μl each of the culture supernatant of the COS-1 cells, and the CHO cells, into which cHGF and dcHGF expression vectors obtained in Example 2 were introduced, was dividedly added to each well. Moreover, the haemolymph obtained in Example 3 was diluted with medium by a factor of 2,000, whereas the supernatant of a cultured insect cells was diluted with the same medium by a factor of 4. Then, 50 μl each of the diluents was further dividedly added to each well. Twenty-four hours after addition of the sample, a 1/10 volume of 25% glutaraldehyde solution (Wako Pure Chemical Industries, Ltd.) was added to fix the cells, and then the motility and the form of the cells were observed by Giemsa stain under microscopy.

All publications, patents and patent applications cited herein are incorporated herein by reference in their entirety.

INDUSTRIAL APPLICABILITY

The present invention provides a cHGF, a 5 amino acids-deleted cHGF thereof, and genes encoding the cHGF and the 5 amino acids-deleted cHGF thereof The recombinant cHGF and the 5 amino acids-deleted cHGF of the present invention are useful for treatment of chronic canine diseases such as canine liver or kidney diseases.

---

The invention claimed is:

1. An isolated recombinant protein having the amino acid sequence of SEQ ID NO: 2 or 4.

2. An isolated DNA or RNA encoding a protein having the amino acid sequence of SEQ ID NO: 2 or 4.

3. An isolated DNA comprising the nucleotide sequence of SEQ ID NO: 1 or 3.

4. A recombinant vector comprising the DNA or RNA according to claim 2.

5. An isolated host cell comprising the recombinant vector according to claim 4.

6. A method for producing a canine hepatocyte growth factor having the amino acid sequence of SEQ ID NO: 2 or 4, which comprises culturing the isolated host cell according to claim 5 and collecting the canine hepatocyte growth factor from the obtained culture.

7. A recombinant vector comprising the DNA according to claim 3.

8. An isolated host cell comprising the recombinant vector according to claim 7.

9. A method of producing a canine hepatocyte growth factor having the amino acid seuuence of SEQ ID NO: 2 or 4, which comprises culturing the isolated host cell according to claim 8 and collecting a canine hepatocyte growth factor from the obtained culture.

10. A probe for detecting a DNA molecule encoding a canine hepatocyte growth factor protein, wherein the probe consists of 200 to 300 nucleotides of the DNA of claim 3.

* * * * *

UNITED STATES PATENT AND TRADEMARK OFFICE
CERTIFICATE OF CORRECTION

| | |
|---|---|
| PATENT NO. | : 7,129,064 B2 |
| APPLICATION NO. | : 10/311776 |
| DATED | : October 31, 2006 |
| INVENTOR(S) | : Masashi Miyake et al. |

It is certified that error appears in the above-identified patent and that said Letters Patent is hereby corrected as shown below:

At item (73) on the title page of the patent, the correct assignee name is "Nippon Zenyaku Kogyo Co., Ltd."

Signed and Sealed this

Nineteenth Day of February, 2008

JON W. DUDAS
*Director of the United States Patent and Trademark Office*